(12) United States Patent
Lee et al.

US010131881B2

(10) Patent No.: US 10,131,881 B2
(45) Date of Patent: Nov. 20, 2018

(54) METHOD FOR PREPARING INDUCED PLURIPOTENCY STEM CELLS FROM MESENCHYMAL STEM CELLS BY USING PHLOROTANNIN FRACTION

(71) Applicant: BBHC, Yongsan-gu, Seoul (KR)

(72) Inventors: Sang Yeon Lee, Uiwang-si (KR); Won Ju Jung, Seoul (KR); Ho Bin Kim, Seoul (KR); Min Sun Oh, Seoul (KR); Kye Ho Lee, Seoul (KR)

(73) Assignee: BBHC, Seoul (KR)

( * ) Notice: Subject to any disclaimer, the term of this patent is extended or adjusted under 35 U.S.C. 154(b) by 35 days.

(21) Appl. No.: 15/116,210

(22) PCT Filed: May 22, 2015

(86) PCT No.: PCT/KR2015/005183
§ 371 (c)(1),
(2) Date: Dec. 12, 2016

(87) PCT Pub. No.: WO2015/178728
PCT Pub. Date: Nov. 26, 2015

(65) Prior Publication Data
US 2017/0107481 A1 Apr. 20, 2017

(30) Foreign Application Priority Data

May 23, 2014 (KR) .................. 10-2014-0062526
May 21, 2015 (KR) .................. 10-2015-0071240

(51) Int. Cl.
*C12N 5/00* (2006.01)
*C12N 5/074* (2010.01)
*C12N 5/0775* (2010.01)
*A61K 31/357* (2006.01)

(52) U.S. Cl.
CPC .......... *C12N 5/0696* (2013.01); *A61K 31/357* (2013.01); *C12N 5/0018* (2013.01); *C12N 5/0668* (2013.01); *C12N 2500/76* (2013.01); *C12N 2501/999* (2013.01); *C12N 2506/025* (2013.01); *C12N 2506/1346* (2013.01); *C12N 2506/1392* (2013.01)

(58) Field of Classification Search
CPC .................. C12N 5/0696; C12N 5/0668
See application file for complete search history.

(56) References Cited

U.S. PATENT DOCUMENTS

2008/0227136 A1* 9/2008 Pla .................. C07K 16/00
                                                      435/29
2010/0021494 A1* 1/2010 Yuasa ................ A61K 36/03
                                                      424/195.17

FOREIGN PATENT DOCUMENTS

| JP | 04146146 | 3/2002 |
| KR | 1011662570000 | 7/2012 |
| KR | 1015441950000 | 8/2015 |
| KR | 1016563880000 | 9/2016 |
| KR | 1018077040000 | 12/2017 |

OTHER PUBLICATIONS

Hwang et al. Int. J. Cancer 119:2742-2749, 2006.*
Ali, et al., "Phlorotannin-incorporated mesenchymal stem cells and their promising role in osteogenesis imperfecta," Journal of Medical Hypotheses, vol. 6,pp. 85-89, 2012.

* cited by examiner

*Primary Examiner* — Marcia S Noble
(74) *Attorney, Agent, or Firm* — McDonnell Boehnen Hulbert & Berghoff LLP

(57) ABSTRACT

The present invention relates to a medium composition for the dedifferentiation of induced pluripotency stem cells, containing a phlorotannin fraction extracted and isolated from one type of brown algae selected from the group consisting of *Ecklonia cava, Dictyopteris prolifera, Dictyota coriacea, Sargassum horneri, Ishige okamurai* and the like. In addition, the present invention relates to a method for preparing induced pluripotency stem cells by using the medium composition. Induced pluripotency stem cells can be safely, easily and effectively prepared by using mesenchymal stem cells by using the medium composition of the present invention, and the prepared induced pluripotency stem cells can be differentiated into various cells, and thus can be useful as a cell therapeutic agent.

6 Claims, 22 Drawing Sheets

METHOD FOR PREPARING INDUCED PLURIPOTENCY STEM CELLS FROM MESENCHYMAL STEM CELLS BY USING PHLOROTANNIN FRACTION

TECHNICAL FIELD

The present invention relates to a medium composition of induced pluripotency stem cells of mesenchymal stem cells containing a phlorotannin fraction extracted from brown algae, and a method for preparing induced pluripotency stem cells using the same.

BACKGROUND ART

Stem cells are cells which may be differentiated into various cells configuring an organism tissue and collectively called undifferentiated cells before differentiation which may be obtained from each tissue of an embryo, a fetal, and an adult. The stem cells may be classified by various methods. One of the most common methods depends to an object with isolated stems cells, and the stem cells may be divided into embryonic stem cells (ES cells) isolated from the embryo and adult stem cells isolated from the adult. Another common classification follows differentiation ability of the stem cells, and the stem cells may be divided into pluripotency, multipotency, and unipotency stem cells. The pluripotency stem cells are called stem cells having multi-function which may be differentiated into three germ layers configuring a living body and generally, embryonic stem cells correspond thereto.

The adult stem cells may be classified into multipotency or unipotency stem cells. Representative adult stem cells include mesenchymal stem cells (MSCs) and hematopoietic stem cells (HSCs). It is known that the MSCs are differentiated into chondroblast, osteoblast, adipocyte, myocyte, and neurion, and the HSCs are differentiated into blood cells in the blood including red blood cells, white blood cells, platelets, and the like. The adult stem cells may be obtained from bone marrow, blood, brain, skin, etc. to have less ethical issues, but have limited multipotency as compared with the embryonic stem cells.

On the other hand, the pluripotency stem cells are called stem cells having multifunction which may be differentiated into three germ layers configuring a living body to be differentiated into all cells or organ tissues of the human body and generally, embryonic stem cells correspond thereto. The embryonic stem cells are pluripotency stem cells having potency which may be differentiated into cells of all tissues configuring one object, but have serious ethical issues in that embryos are broken in the cell preparing process.

As an alternative for solving the problems, various methods for preparing customized pluripotency stem cells similar to the embryonic stem cells by dedifferentiating cells derived from the adult have been attempted. It is known that the human embryonic stem cells are made from the embryos which may be generated to the human organism, and thus, there are many ethical issues, but the embryonic stem cells have excellent cell proliferation and multipotency as compared with the adult stem cells. The adult stem cells may be obtained from bone marrow, blood, brain, skin, etc. to have less ethical issues, but have limited multipotency as compared with the embryonic stem cells.

As a representative method, there are methods, for example, a fusion with ES cell, a somatic cell nuclear transfer, a reprogramming by gene factor and the like. The fusion with ES cell has a problem in terms of cell stability because the induced cells further have two pairs of genes, and the somatic cell nuclear transfer has a problem in that a lot of ova are required and efficiency is too low. In addition, the reprogramming by gene factor is a method using virus containing oncogenes in order to induce dedifferentiation by inserting specific genes, and thus, has a high risk of cancer occurrence, and also, has a problem in terms of development of cell therapeutic agents due to low efficiency and difficulty in a methodical aspect.

In order to successfully obtain a large amount of pluripotency stem cells, a culture composition is very important in the culturing of mononuclear cells derived from isolated umbilical cord, and thus researches for preparing a larger amount of pluripotency stem cells by an induction method with high efficiency are required.

Meanwhile, in Korea Patent Publication No. 2009-0043115, a composition for treating or preventing atopic diseases by using *Ecklonia cava* of brown algae is disclosed, and in Korea Patent Publication No. 2012-0126148, a hairdye composition for oxidation dyeing is disclosed.

The present inventors successfully develop a medium composition for dedifferentiation of induced pluripotency stem cells by using an *Ecklonia cava* extract (Korea Patent Publication No. 2015-0050823). However, which component of the *Ecklonia cava* extract has a dedifferentiation effect of the induced pluripotency stem cells has been not yet known.

Details described in the background are only for enhancement of understanding of the background of the present invention and therefore it may contain information that does not form the prior art that is already known in this country to a person of ordinary skill in the art.

DISCLOSURE

Technical Problem

The present inventors made efforts to find a method of inducing pluripotency stem cells with high efficiency in order to commercialize development of cell therapeutic agents with high stability and high production efficiency. As a result, the inventors verified that when some compounds extracted and isolated from brown algae as a stable natural substance were added in the cell culture medium, the induced pluripotency stem cells may be prepared with stability and high efficiency by using mesenchymal stem cells, and thus, completed the present invention.

The present invention is directed to provide a medium composition for dedifferentiating mesenchymal stem cells containing a phlorotannin fraction into induced pluripotency stem cells.

The present invention is also directed to provide a method for preparing induced pluripotency stem cells comprising dedifferentiating pluripotency stem cells into induced pluripotency stem cells in a medium containing a phlorotannin fraction. Further, the present invention is also directed to provide a cell therapeutic composition including induced pluripotency stem cells prepared by the preparing method. Other objects and advantages of the present invention are clearer by the detailed description of the invention, claims, and drawings to be described below.

Technical Solution

An aspect of the present invention provides a medium composition for dedifferentiating mesenchymal stem cells containing a phlorotannin fraction into induced pluripotency stem cells.

Preferably, the phlorotannin fraction may be a bieckol compound represented by the following Chemical Formula 1 or salts thereof.

[Chemical Formula 1]

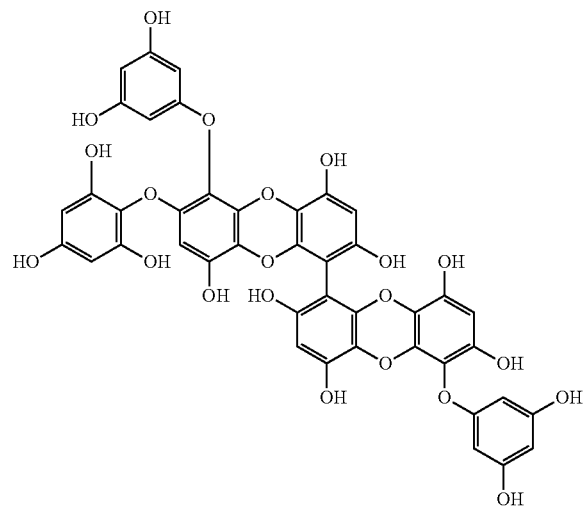

Preferably, the phlorotannin fraction may be extracted and isolated from one type of brown algae selected from the group consisting of *Ecklonia cava, Dictyopteris prolifera Okamura, Dictyota dichotoma Lamouroux, Sargassum horneri C. Agardh, Sargassum patens C. Agardh*, and *Ishige okamurae Yendo*, or artificially synthesized.

Preferably, the phlorotannin fraction may be extracted and isolated from *Ecklonia cava*.

Preferably, the phlorotannin fraction may be included in a medium selected from the group consisting of DMEM (Dulbecco's Modified Eagle's Medium), MEM (Minimal Essential Medium), BME (Basal Medium Eagle), RPMI 1640, F-10, F-12, DMEM F-12, α-MEM (α-Minimal Essential Medium), G-MEM (Glasgow's Minimal Essential Medium), IMDM (Iscove's Modified Dulbecco's Medium), MacCoy's 5A Medium, AminoMaxII complete Medium, and MesenCult-XF Medium.

Preferably, the phlorotannin fraction may be included in the amount of 10 to 500 μg/ml with respect to the medium composition.

Preferably, the medium composition may additionally include 1 to 10 v/v % of energy water.

Another aspect of the present invention provides a method for preparing induced pluripotency stem cells comprising: adding a phlorotannin fraction in a cell culture medium; and dedifferentiating mesenchymal stem cells into induced pluripotency stem cells in the medium.

Preferably, the phlorotannin fraction may be a bieckol compound represented by the following Chemical Formula 1 or salts thereof.

[Chemical Formula 1]

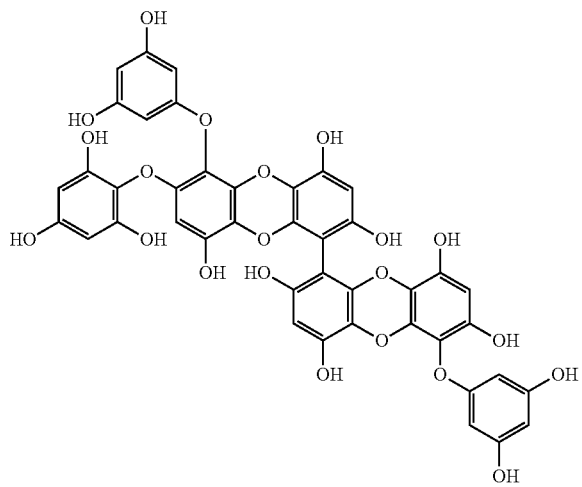

Preferably, yet another aspect of the present invention provides a cell therapeutic composition containing the induced pluripotency stem cells prepared by the method Advantageous Effects Features and advantages of the present invention are as follows.

(i) The present invention provides a medium composition for the dedifferentiation of induced pluripotency stem cells by using a phlorotannin fraction extracted from brown algae.

(ii) Further, the present invention provides a method for preparing induced pluripotency stem cells using the medium composition.

(iii) Induced pluripotency stem cells can be effectively prepared by using mesenchymal stem cells by using the medium composition of the present invention, and the prepared induced pluripotency stem cells can be differentiated into various cells, and thus can be useful as a cell therapeutic agent.

MODES OF THE INVENTION

Figure 1:
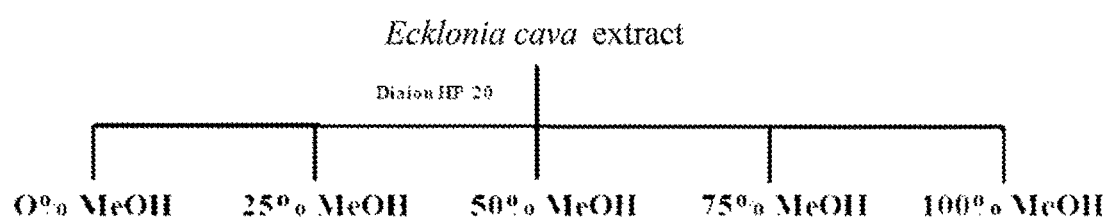
FIG. 1 illustrates a condition for isolating a fraction from an *Ecklonia cava* extract.

According to an aspect of the present invention, the present invention provides a medium composition for dedifferentiating mesenchymal stem cells containing a phlorotannin fraction extracted and isolated from brown algae into induced pluripotency stem cells.

The present inventor made an effort to find a method of inducing pluripotency stem cells with high efficiency in order to commercialize development of cell therapeutic agents with stability and high production efficiency without an ethical issue in breakage of embryos. As a result, it is verified that when a phlorotannin fraction isolated from a brown algae extract as a stable natural extract, preferably, an *Ecklonia cava* extract is added to a cell culture medium, amazingly, the induced pluripotency stem cells may be prepared with high efficiency.

According to an exemplary embodiment of the present invention, the brown algae extract may be a brown algae-water extract, a brown algae-ethanol extract, a brown algae-methanol extract, or a brown algae extract using a mixed solvent of two or more selected from water, ethanol, and methanol.

According to the exemplary embodiment of the present invention, the brown algae-water extract may be prepared by extracting the brown algae with water of 40 to 100° C. for 2 to 48 hours. The brown algae-ethanol extract may be prepared by extracting the brown algae with 35 to 80% ethanol at 20 to 60° C. for 2 to 36 hours. Further, the brown algae-methanol extract may be prepared by extracting the brown algae with 35 to 80% methanol at 20 to 60° C. for 2 to 36 hours.

*Ecklonia cava* among the brown algae included in the medium composition of the present invention is a perennial alga of a laminariaceous laminariales brown plant that mainly lives in the southern coast, the coast of the Jeju Island, and the coast of the Ulleungdo island, mainly becomes food for abalone, turban, and the like, and used as the main raw material to make alginate or potassium iodide or for food.

The *Ecklonia cava* extract included in the present invention may be extracted by using water and organic solvents including (a) anhydrous or water-containing low alcohol having 1 to 4 carbons (methanol, ethanol, propanol, butanol, n-propanol, iso-propanol, n-butanol, etc.), (b) a mixed solvent of the low alcohol and water, (c) acetone, (d) ethyl acetate, (e) chloroform, (f) 1,3-butylene glycol, (g) hexane, (h) diethyl ether, and the like, and preferably, may be extracted by using a mixed solvent of methanol or ethanol and water. In the case of extracting the *Ecklonia cava* extract by using the mixed solvent, the content of methanol or ethanol may be 50 to 80 v/v %. However, the present invention is not necessarily limited thereto.

Phlorotannin isolated from the brown algae extract is a polyphenol-based compound containing phloroglucinol as a basic constituent unit. The phlorotannin is found in a lot of marine plants, particularly, brown algae in the natural world, and it is reported that the phlorotannin has various useful effects such as an antibacterial effect, an antioxidant effect, a hepatoprotective activity, an elastase inhibition activity, a hyaluronidase inhibition activity, a cardiovascular protection effect, and an anti-viral activity.

In the present invention, particularly, a bieckol compound represented by the following Chemical Formula 1, a dieckol compound represented by the following Chemical Formula 2, a phlorofucofuroeckol compound represented by the following Chemical Formula 3, an eckol-based compound represented by the following Chemical Formula 4, and an eckol-based compound represented by the following Chemical Formula 5 are isolated and identified from the phlorotannin fraction of the *Ecklonia cava* extract, and expression ability of induced pluripotency stem cells thereof is verified. When the bieckol compound represented by the following Chemical Formula 1 among the compounds is added in the cell culture medium, it is verified that the induced pluripotency stem cells can be prepared with high efficiency.

[Chemical Formula 1]

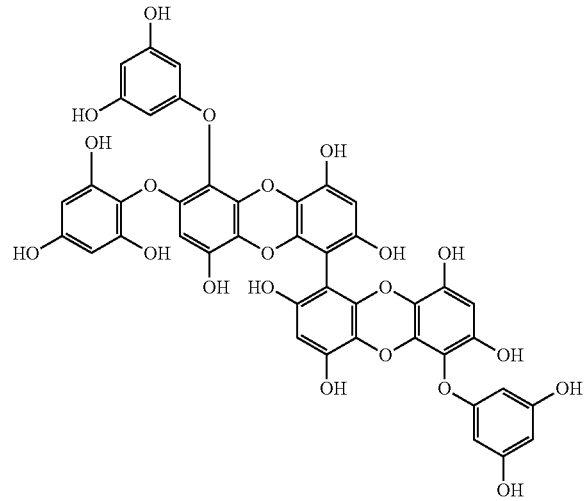

[Chemical Formula 2]

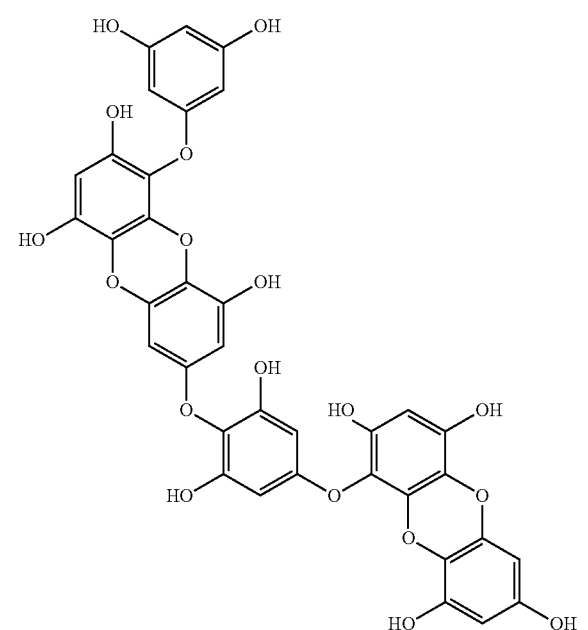

[Chemical Formula 3]

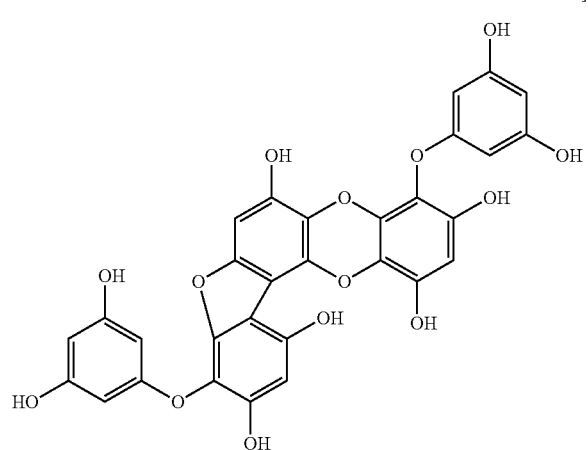

[Chemical Formula 4]

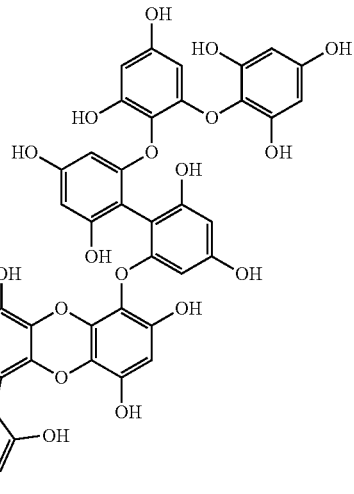

[Chemical Formula 5]

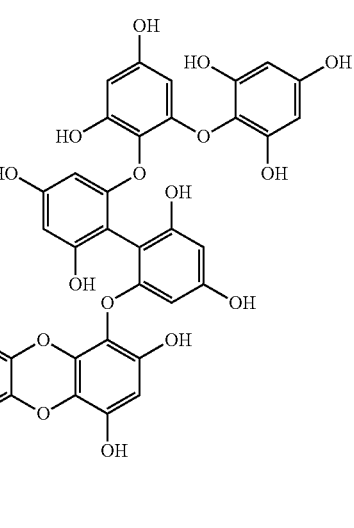

More particularly, Chemical Formula 1 is represented by 2-O-(2,4,6-trihydroxyphenyl)-6,6'-bieckol, Chemical Formula 2 is represented by dieckol, Chemical Formula 3 is represented by phlorofucofuroeckol-A (PFF-A), Chemical Formula 4 is represented by 974-A, and Chemical Formula 5 is represented by 974-B, and in the present invention, the compounds may be added in the cell culture medium alone or in combination thereof.

The term "embryonic stem cells" used in the present invention are called cells having pluripotency as cells which are isolated and cultured from an inner cell mass of blastocyst in the early days of its development after fertilization. The term "pluripotency stem cells" used in the present invention are called stem cells having pluripotency which may be differentiated into three germ layers configuring the adult, that is, an endoderm, a mesoderm, and an ectoderm.

The term "differentiation" used in the present invention means that while the cells are divided, proliferated, and grown, structures or functions thereof are specialized, that is, forms or functions are changed in order to perform tasks which are given to cells, tissues, and the like of an organism.

The term "cellular therapeutic agent" of the present invention, as a drug used for treating, diagnosing, and preventing by using cells and tissues prepared through isolation from the human, culture, and a specific manipulation, means a drug used for treating, diagnosing, and preventing through a series of actions such as proliferating and screening homogenous or heterogeneous cells for restoring functions of cells or tissues, changing a biological characteristic of the cells by another method, and the like. The cell therapeutic agent is largely classified into a somatic cell therapeutic agent, a stem cell therapeutic agent according to differentiation of the cells, and the present invention particularly relates to the stem cell therapeutic agent.

The mesenchymal stem cells of the present invention are cells isolated from embryonic stem cells or adult stem cells derived from mammalian, preferably mesenchymal stem cells derived from umbilical cord, and more preferably mesenchymal stem cells derived from human umbilical cord. The stem cells may be extracted and obtained from the umbilical cord that connects the placenta and the fetus in the human body. The extraction of the mesenchymal stem cells from the umbilical cord may be performed by using various methods, and for example, the umbilical cord is extracted from the human body to be washed with DPBS until the blood does not flow, and the washed umbilical cord is chopped with a surgical blade and incubated at 37° C. to obtain a solution containing mononuclear cells.

The term "medium" used in the present invention means a mixture for culturing or differentiating cells such as stem cells in vitro, which contains required elements for growth and proliferation of the cell including sugars, amino acids, various nutrients, serum, growth factors, minerals, and the like.

Various media are commercialized in the art and may be artificially prepared and used. As the commercialized medium, DMEM (Dulbecco's Modified Eagle's Medium), MEM (Minimal Essential Medium), BME (Basal Medium Eagle), RPMI 1640, F-10, F-12, DMEM F-12, α-MEM (α-Minimal Essential Medium), G-MEM (Glasgow's Minimal Essential Medium), IMPM (Iscove's Modified Dulbecco's Medium), AmnioMax, AminoMaxII complete Medium (Gibco, Newyork, USA), MesenCult-XF Medium, and the like are included, and may be used as a basic medium included in a medium composition in addition to the medium which may be artificially prepared.

In the basic medium, generally added serum components (for example, fetal bovine serum (FBS)), antibiotics (for example, penicillin and streptomycin), and the like may be added. The concentration of the serum component or the antibiotic component which is added in the basic medium may be modified within a range that can achieve the effect of the present invention, and preferably, 10% FBS, 100 unit/ml penicillin, 50 µg/ml streptomycin, and the like may be added.

Meanwhile, the concentration of the compound added to the DMEM may be modified within a range that can achieve the effect of the present invention.

Further, the medium of the present invention may additionally include a nutrient mixture. The nutrient mixture is a mixture containing various amino acids, vitamins, inorganic salts, and the like which are generally used in a cell culture and may use a nutrient mixture which is prepared by mixing the amino acids, the vitamins, the inorganic salts, and the like or commercially prepared. The commercially prepared nutrient mixture may include M199, MCDB110, MCDB202, MCDB302, and the like as an example, but is not limited thereto.

Further, the medium of the present invention may additionally include energy water for induction and stabilization of the pluripotency stem cells. The energy water is preferably added with 0.05 to 20 v/v % and more preferably 0.1 to 10 v/v %.

The medium composition of the present invention is a specific medium to induction of the pluripotency stem cells and may be achieved by adding a phlorotannin fraction isolated from the brown algae extract in the basic medium, and may include a phlorotannin fraction isolated from an *Ecklonia cava* extract preferably at a concentration of 1 to 1,000 µg/ml and more preferably at a concentration of 10 to 50 µg/ml with respect to the entire medium composition. Further, at least one type selected from a group consisting of 2-O-(2,4,6-trihydroxyphenyl)-6,6'-bieckol of Chemical Formula 1, dieckol of Chemical Formula 2, phlorofucofuroeckol-A (PFF-A) of Chemical Formula 3, 974-A of Chemical Formula 4, and 974-B of Chemical Formula 5 may be used at 10 to 200 µg/ml, more preferably 20 to 150 µg/ml with respect to the entire medium composition.

According to another aspect of the present invention, the present invention provides a method for preparing induced pluripotency stem cells including: adding a phlorotannin fraction isolated from an *Ecklonia cava* extract in a cell culture medium; and dedifferentiating mesenchymal stem cells into induced pluripotency stem cells in the medium.

In the case, umbilical cord-derived mononuclear cells are added in the basic medium composition containing 2-O-(2, 4,6-trihydroxyphenyl)-6,6'-bieckol or a mixture containing 2-O-(2,4,6-trihydroxyphenyl)-6,6'-bieckol and may be incubated in an incubator under a condition of humidity 95%, 37° C., and 5% $CO_2$.

In an exemplary embodiment of the present invention, the umbilical cord-derived mononuclear cells are incubated in the incubator under the condition and then a cell supernatant is removed after 5 days, and the cells are incubated by replacing the medium every 3 to 4 days. When the stem cells are incubated by using the culture medium composition containing 2-O-(2,4,6-trihydroxyphenyl)-6,6'-bieckol, induction of the pluripotency stem cells according to a concentration of 2-O-(2,4,6-trihydroxyphenyl)-6,6'-bieckol is observed. A DMEM F-12 medium is used as a control group and a medium containing —O-(2,4,6-trihydroxyphenyl)-6,6'-bieckol in the DMEM F-12 medium is used as an experimental group and mesenchymal stem cells derived from human umbilical cord are incubated in the medium treated for each concentration.

Figure 17:
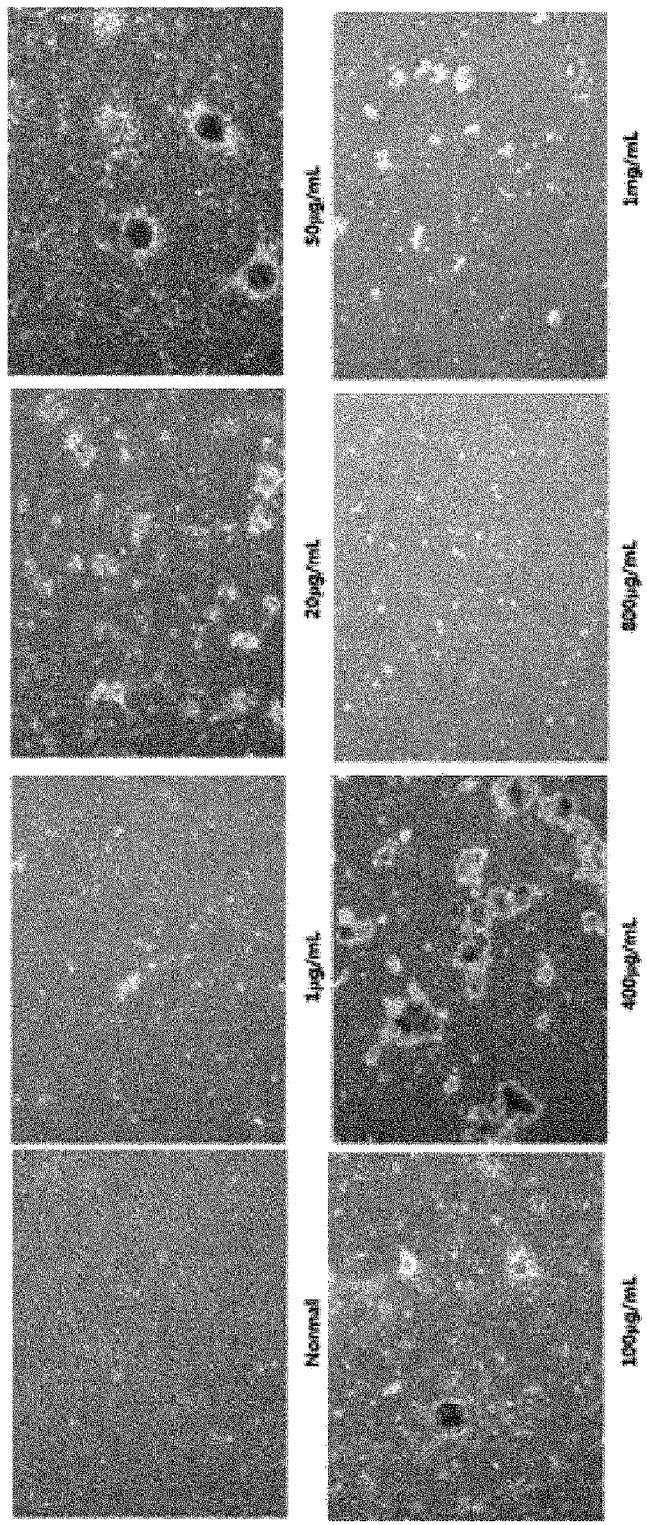
FIG. 17 illustrates formation of induced pluripotency stem cell colonies according to a concentration by treating a phlorotannin fraction of an *Ecklonia cava* extract by using a method (Experimental Example 1-1) of the present invention.

As a result, it can be seen that when the mesenchymal stem cells are incubated in the medium composition of the present invention, colonies such as pluripotency stem cells are formed. The mesenchymal stem cells derived from the human umbilical cord form stem cell colonies in the medium of the present invention at 10 to 14 days. That is, it can be seen that the culture medium composition of the present invention forms pluripotency stem cell colonies from the mesenchymal stem cells derived from the human umbilical cord (see FIGS. 17 to 19).

According to yet another aspect of the present invention, the present invention provides induced pluripotency stem cells prepared by the preparing method.

The induced pluripotency stem cells of the present invention have the same differentiation as the embryonic stem cells and are almost the same as the embryonic stem cells even in shapes of the cells. According to the exemplary embodiment of the present invention, whether to express a specific gene (Nanog, Oct4, Sox2, Klf) and protein (SSEA-4) to the embryonic stem cells is examined, and as a result, it can be seen that the gene and the protein are expressed in the pluripotency stem cells induced by the present invention like the embryonic stem cells (see FIG. 19).

According to still another aspect of the present invention, the present invention provides a cell therapeutic composition containing the induced pluripotency stem cells prepared by the preparing method.

It can be seen that the induced pluripotency stem cells of the present invention have the same pluripotency as the embryonic stem cells, and according to the exemplary embodiment of the present invention, have pluripotency which may be differentiated into an ectoderm, a mesoderm, and an endoderm.

Accordingly, the induced pluripotency stem cells of the present invention may be used as an effective cell therapeutic agent.

The composition of the present invention may be administrated by any administration route, particularly, a method such as peritoneal or thoracic cavity administration, subcutaneous administration, intravenous or endovascular administration, intramuscular administration, local administration by injection, or the like.

In the present invention, the composition may be administrated in a form such as Injections, suspensions, and emulsions on the basis of a general method, and if necessary, may be suspended in an adjuvant such as a freund complete adjuvant or administrated together with a material having an adjuvant activity such as BCG. The composition is sterilized or may contain adjuvants including stabilizers, wetting or emulsifying accelerators, salts or buffers for adjusting the osmotic pressure, and the like and other therapeutically valuable substances, and may be prepared by a general mixing, granulating, or coating method.

The cell therapeutic composition according to the present invention may contain pharmaceutically acceptable carriers or additives, and may contain diluents (e.g., dextrose, sorbitol, cellulose, glycine, lactose, sucrose, and mannitol), binders (e.g., magnesium aluminum silicate, starch paste, tragacanth, sodium carboxymethyl cellulose), disintegrants (e.g., starch, agar, alginic acid, or sodium salts thereof), or a boiling mixture and/or absorbent agents, sweetening agents, flavoring agent, and coloring agents, in addition to active ingredients.

The cell therapeutic composition according to the present invention can be applied to arthritis, neurological disorders, endocrine disorders, liver diseases, and the like and has a possibility to an allogenic therapeutic agent for the human according to clinical trial results for the human later.

Hereinafter, the present invention will be described in more detail through Examples. However, the present invention is not limited to the exemplary embodiments disclosed below, but can be implemented in various forms. The following exemplary embodiments are described in order to enable those of ordinary skill in the art to embody and practice the invention.

EXAMPLES

Example 1: Preparation of Phlorotannin Fraction and Compounds of Chemical Formulas 1 to 5

Example 1-1: Preparation of Phlorotannin Fraction from *Ecklonia cava* Extract

Herb medicine samples used in an experiment were purchased in the Jeju Island, received an evaluation of the expert, and used in the experiment. 100 g of a dried herb medicine sample was added in 1 L of 70% methanol, reflux-extracted for 16 hours, and filtrated by using a filter. A filtrate was concentrated in a rotary decompression evaporator and immediately freeze-dried to prepare an *Ecklonia cava* extract.

5 g of the *Ecklonia cava* extract was dissolved with 500 µl methanol, absorbed on a C4 resin (Sepia tech), decompression-dried at 30° C. by using a rotary vacuum evaporator, and divided for each solvent by using Diaion HP-20 for small fractions. Gradient was given and methanol solvents having concentrations of 0%, 25%, 50%, 75% and 100% were prepared to perform the fraction. 5 small fractions are divided and a HPLC profile was verified (see FIG. 1). A fraction having the highest HPLC peak among the five small fractions was selected.

Example 1-2: Isolation and Purification of Phlorotannin Fraction

The fractions obtained in Example 1-1 were applied to C-18 reverse-phased HPLC having a 60 min solvent gradient condition of acetonitrile 10 min, 20 to 55% acetonitrile 40 min, and 55 to 100% acetonitrile 10 min by using a C18 column (Phenomenex Luna C18 equipment, 10 µm, 21.2× 250 mm) and using solvents of acetonitrie containing 0.02% TFA and water at a flow rate 10 ml/min and UV 243 nm to be isolated into peaks C (RT 25 min), E (RT 33 min), G (RT 37.5 min), H (RT 38 min), and I (RT 38.5 min). A fraction from retention time 0 to peak C was called c, a fraction between the peak C and the peak E was called D, a fraction between the peaks E and G was called F, and a fraction after the peak I was called J.

Each peak was purified by using C18 column (Phenomenex Luna C18 equipment, 10 µm, 21.2×250 mm), using solvents of acetonitrie containing 0.02% TFA, methanol, and water at a flow rate 4 ml/min and UV 230 nm under each isocratic condition. Under an acetonitrile 28% isocratic condition, the peak E (RT 10 min), the peak G (RT 22 min), the peak H (RT 23 min), and the peak I (RT 27 min) were purified, respectively.

However, as an analysis result after purification, it was verified that in the peak C, two substances were mixed, and then the two substances ware re-isolated into C-1 (RT 10 min) and C-2 (RT 13.5 min) under a methanol 26% isocratic condition.

Example 1-3: Structural Analysis of Polyphenol-Based Compound

The molecular weight and the molecular formula of the compound purified in Example 1-2 were determined by using a high-performance liquid chromatography mass chromatography (HPLC-MS) and the structural identification of the compound was performed by analyzing $^1$H NMR and $^{13}$C-NMR spectrums through nuclear magnetic resonance (NMR).

As a result, it was identified that Chemical Formula 1 was 2-O-(2,4,6-trihydroxyphenyl)-6,6'-bieckol, Chemical Formula 2 was Dieckol, Chemical Formula 3 was phlorofucofuroeckol-A, Chemical Formula 4 was 974-A, Chemical Formula 3 was 974-B. The structure of the isolated polyphenol-based compound was illustrated in the following Table 1 and structural features of each compound were as follows.

TABLE 1

| Comp No. | Comp. Code | Retention time (min) | Material name |
|---|---|---|---|
| C-1 | Chemical Formula 1 | STC-C-1 | 11.0 | 2-O-(2,4,6-trihydroxyphenyl)-6,6'-bieckol |
| E | Chemical Formula 2 | STC-E | 12.7 | dieckol |
| G | Chemical Formula 3 | STC-G | 13.9 | phlorofucofuroeckol-A |
| H | Chemical Formula 4 | STC-H | 14.2 | 974-B |
| I | Chemical Formula 5 | STC-I | 14.5 | 974-A |

[Chemical Formula 1] 2-O-(2,4,6-trihydroxyphenyl)-6,6'-bieckol

1) Molecular weight: 866.65
2) Molecular formula: C42H26O21
3) $^1$H NMR (400 MHz, DMSO) δ 9.28, 9.25, 9.14, 9.09, 9.06, 9.04, 8.95, 8.66, 8.61, 6.09, 6.07, 6.05, 5.91 (d, J=2.0 Hz, 1H), 5.84, 5.80, δ, 5.75 (d, J=2.0 Hz, 1H).
4) $^{13}$C NMR (100 MHz, dmso) δ 160.6, 160.5, 158.9, 158.9, 154.8, 151.5, 151.4, 151.2, 147.4, 146.5, 144.6, 144.6, 141.7, 141.6, 141.5, 141.5, 137.4, 137.4, 125.0, 123.9, 123.0, 123.0, 122.8, 122.3, 122.3, 99.9, 99.8, 98.1, 98.1, 98.0, 96.2, 96.2, 96.1, 95.0, 94.3, 94.1.

Figure 2:
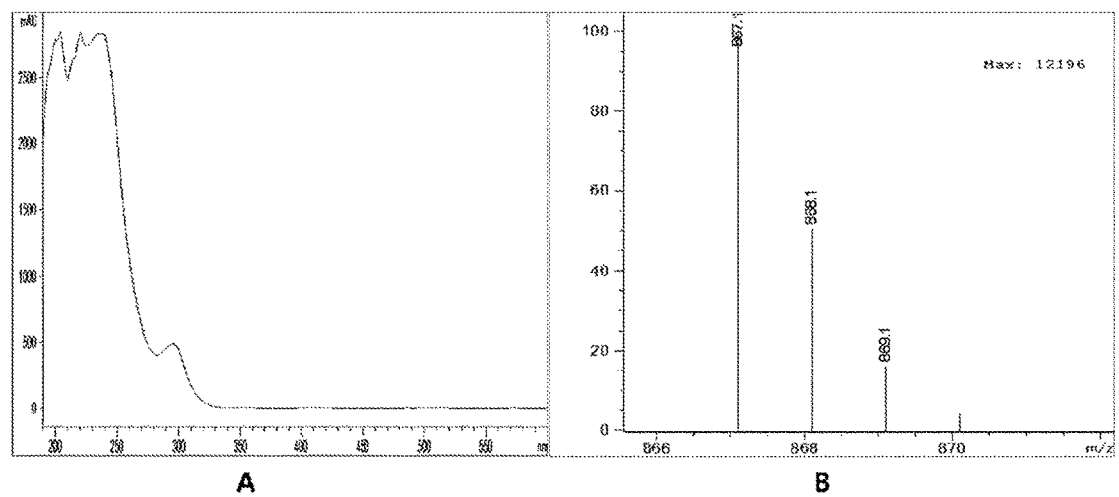
FIG. 2 illustrates a mass spectrum result of 2-O-(2,4,6-trihydroxyphenyl)-6,6'-bieckol represented by Chemical Formula 1.
Figure 3:
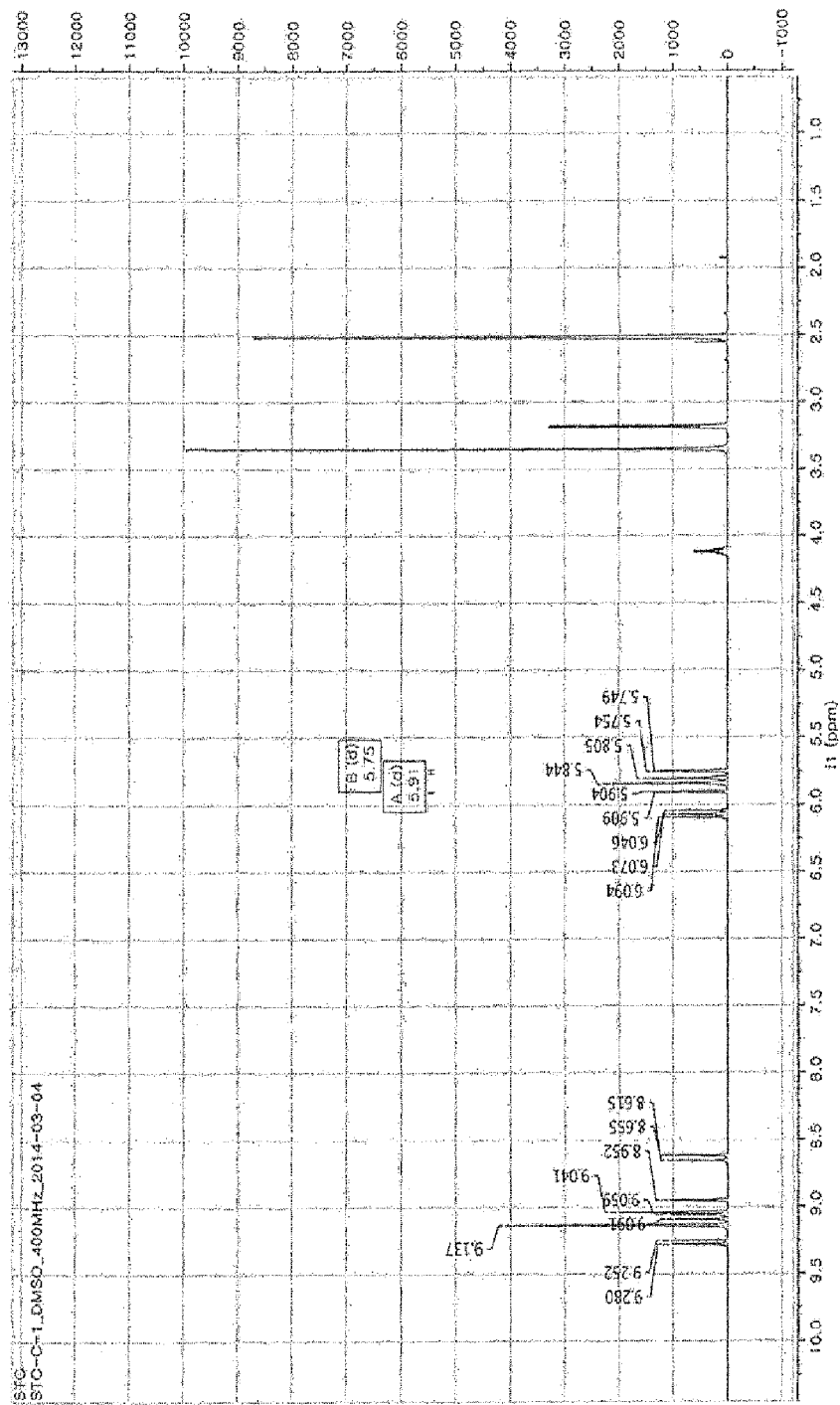
FIG. 3 illustrates a $^1$H-NMR spectrum result of 2-O-(2,4,6-trihydroxyphenyl)-6,6'-bieckol represented by Chemical Formula 1.
Figure 4:
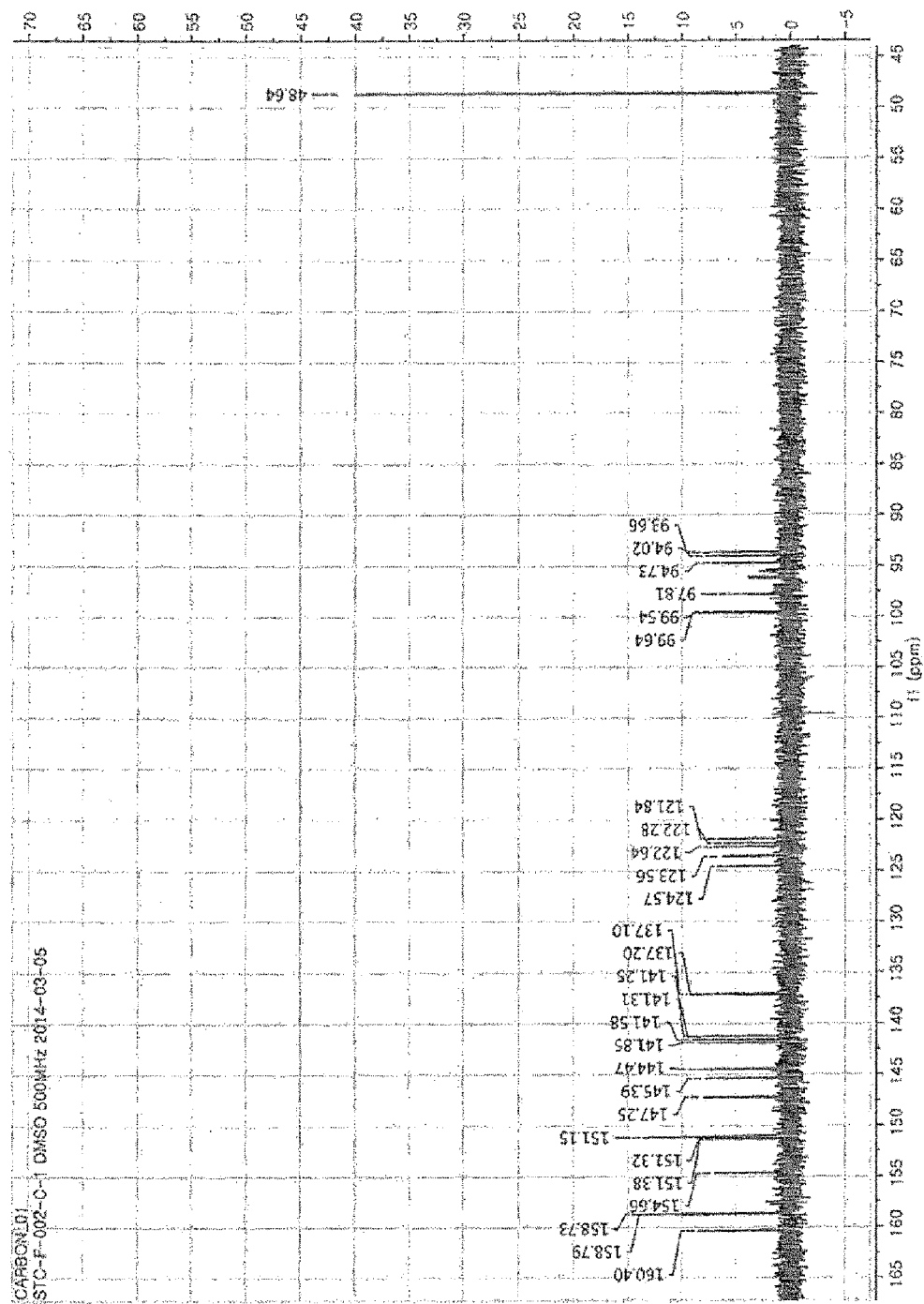
FIG. 4 illustrates a $^{13}$C-NMR spectrum result of 2-O-(2,4,6-trihydroxyphenyl)-6,6'-bieckol represented by Chemical Formula 1.

FIG. 2 illustrates a mass spectrum of the 2-O-(2,4,6-trihydroxyphenyl)-6,6'-bieckol. Further, FIGS. 3 and 4 illustrate a $^1$H-NMR spectrum and a $^{13}$C-NMR spectrum of the 2-O-(2,4,6-trihydroxyphenyl)-6,6'-bieckol, respectively, and figures indicated in each peak corresponds to figures indicated in Chemical Formulas of FIGS. 3 and 4.

[Chemical Formula 2] Dieckol

1) Molecular weight: 742.08
2) Molecular formula: C36H22O18
3) $^1$H NMR (400 MHz, MeOD) δ 6.16 (s, 1H), 6.14 (s, 1H), 6.10 (s, 2H), 6.07 (d, J=2.9 Hz, 1H), 6.06 (d, J=2.9 Hz, 1H), 5.99 (d, J=2.8 Hz, 1H), 5.96 (d, J=2.8 Hz, 1H).
4) $^{13}$C NMR (125 MHz, MeOD) δ 162.70, 160.95, 160.91, 158.63, 156.82, 155.34, 153.22, 148.17, 148.13, 147.97, 147.75, 145.11, 144.95, 144.22, 144.13, 139.46, 139.29, 127.22, 126.98, 126.42, 126.37, 125.66, 125.40, 125.34, 100.65, 100.51, 100.25, 100.14, 98.44, 96.99, 96.63, 96.55, 96.15.

Figure 5:
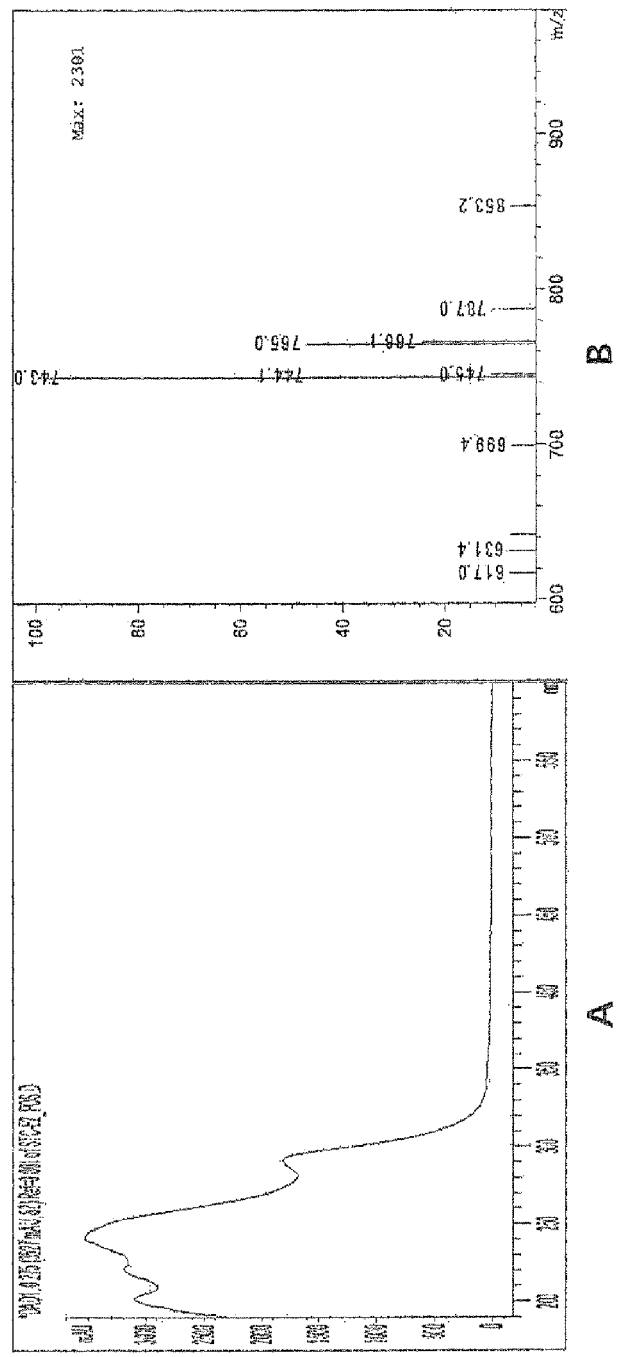
FIG. 5 illustrates a mass spectrum result of dieckol represented by Chemical Formula 2.
Figure 6:
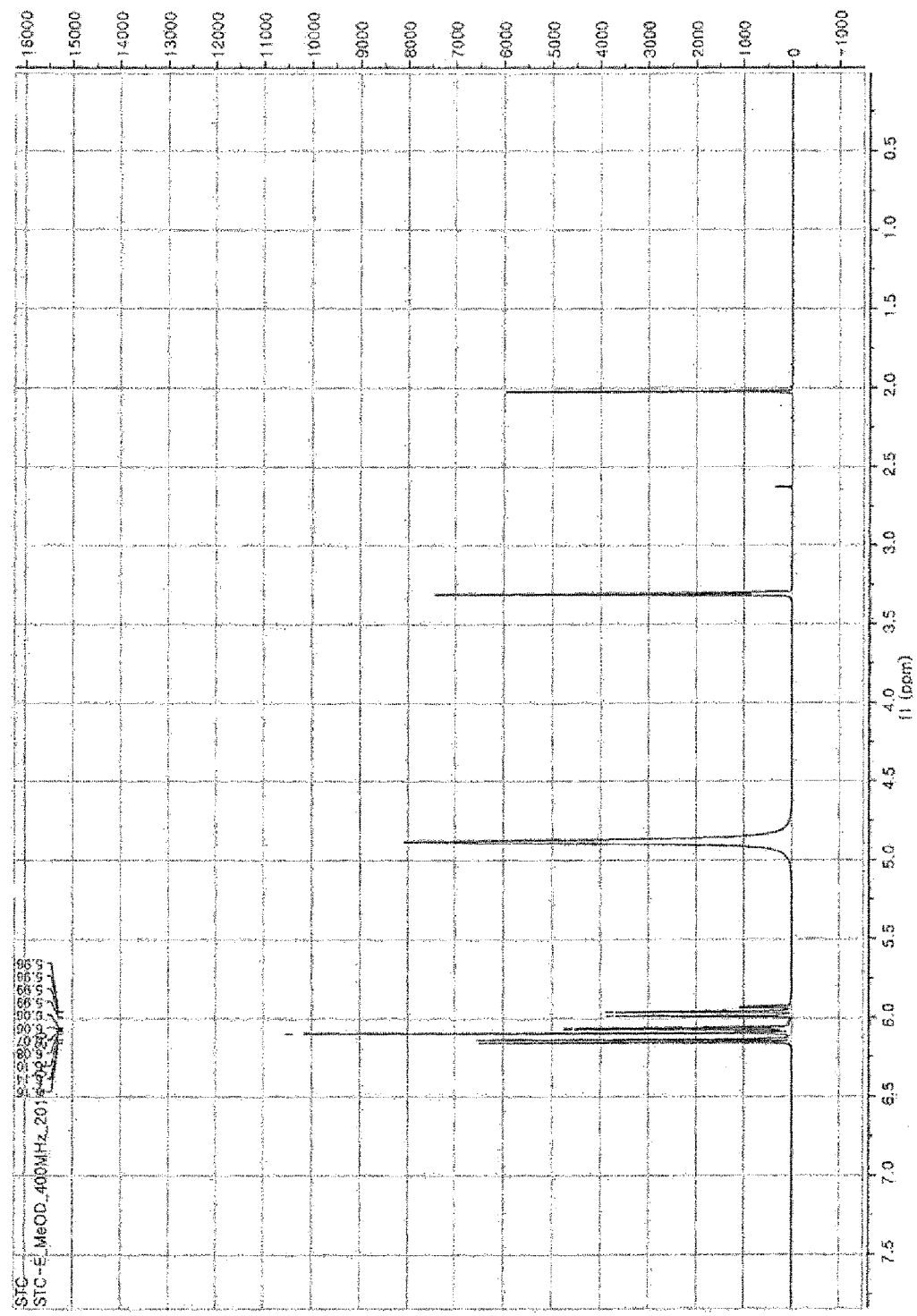
FIG. 6 illustrates a $^1$H-NMR spectrum result of dieckol represented by Chemical Formula 2.
Figure 7:
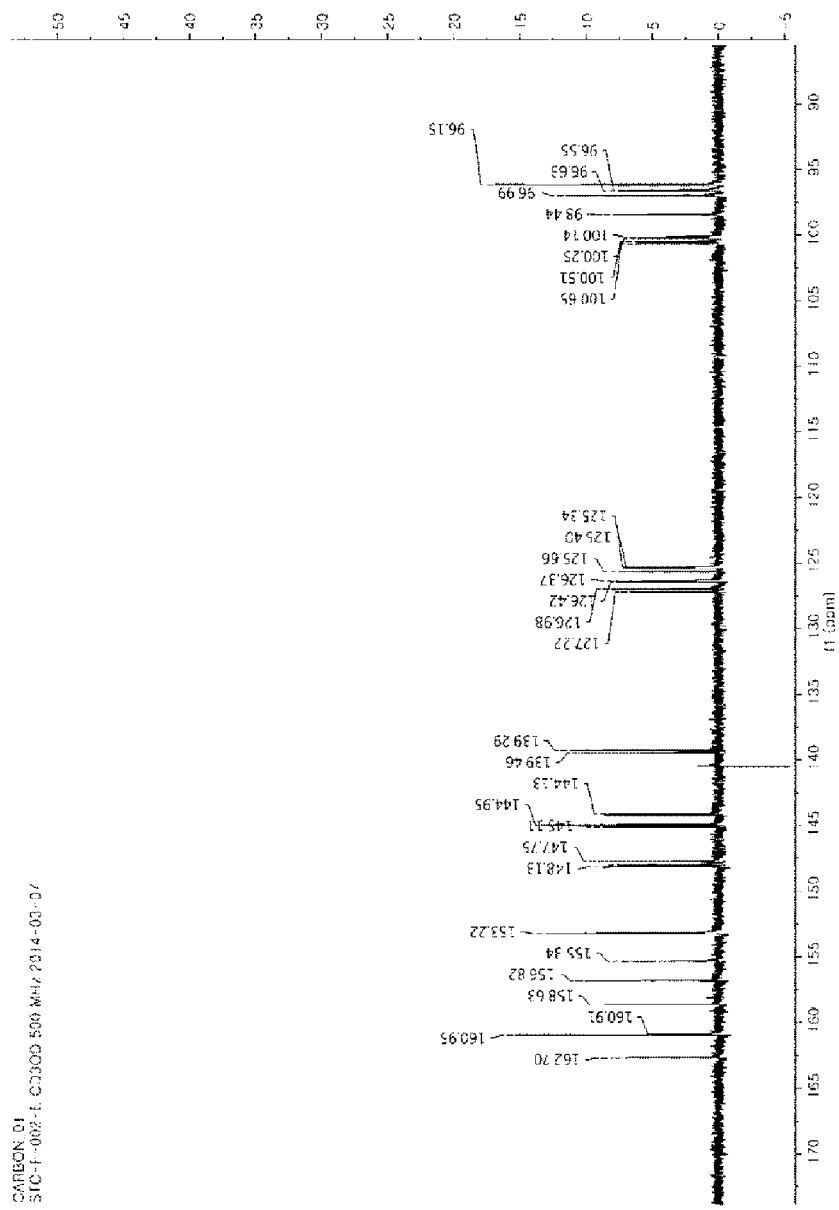
FIG. 7 illustrates a $^{13}$C-NMR spectrum result of dieckol represented by Chemical Formula 2.

FIG. 5 illustrates a mass spectrum of the dieckol. Further, FIGS. 6 and 7 illustrate a $^1$H-NMR spectrum and a 13C-NMR spectrum of the dieckol, respectively, and figures indicated in each peak corresponds to figures indicated in Chemical Formulas of FIGS. 6 and 7.

[Chemical Formula 3] phlorofucofuroeckol-A

1) Molecular weight: 602.07
2) Molecular formula: C30H18O14
3) $^1$H NMR (400 MHz, MeOD) δ 6.63 (s, 1H), 6.40 (s, 1H), 6.26 (s, 1H), 5.96 (d, J=2.1 Hz, 2H), 5.955.93 (t.like, 1H), 5.92 (t, J=2.1 Hz, 1H), 5.88 (d, J=2.1 Hz, 2H).
4) $^{13}$C NMR (125 MHz, MeOD) δ 161.87, 161.84, 160.18, 153.15, 151.73, 151.15, 148.31, 148.21, 145.97, 143.92, 138.37, 135.29, 128.04, 124.94, 124.64, 122.27, 105.29, 99.91, 99.28, 97.69, 97.57, 96.18, 95.35, 95.29.

Figure 8:
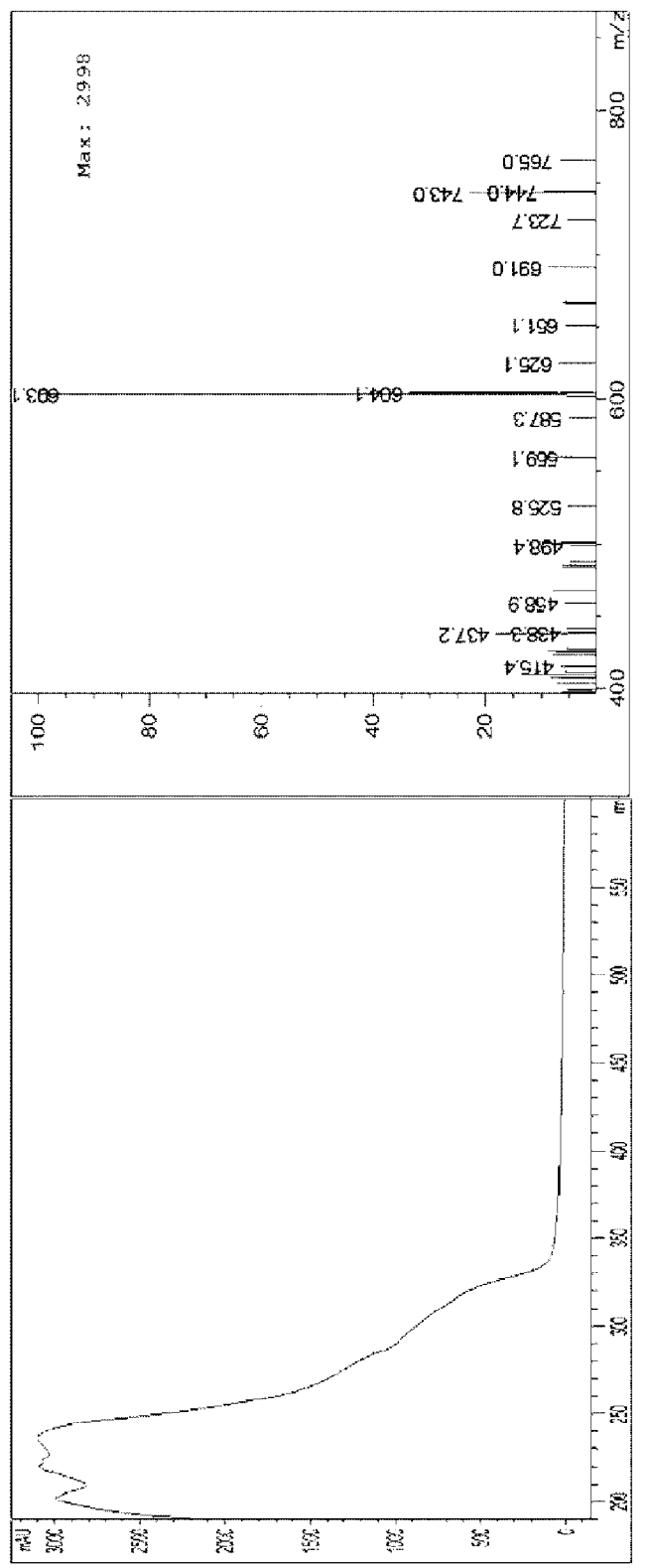
FIG. 8 illustrates a mass spectrum result of phlorofucofuroeckol-A (PFF-A) represented by Chemical Formula 3.

FIG. 8 illustrates a mass spectrum of phlorofucofuroeckol-A (PFF-A).

Figure 9:
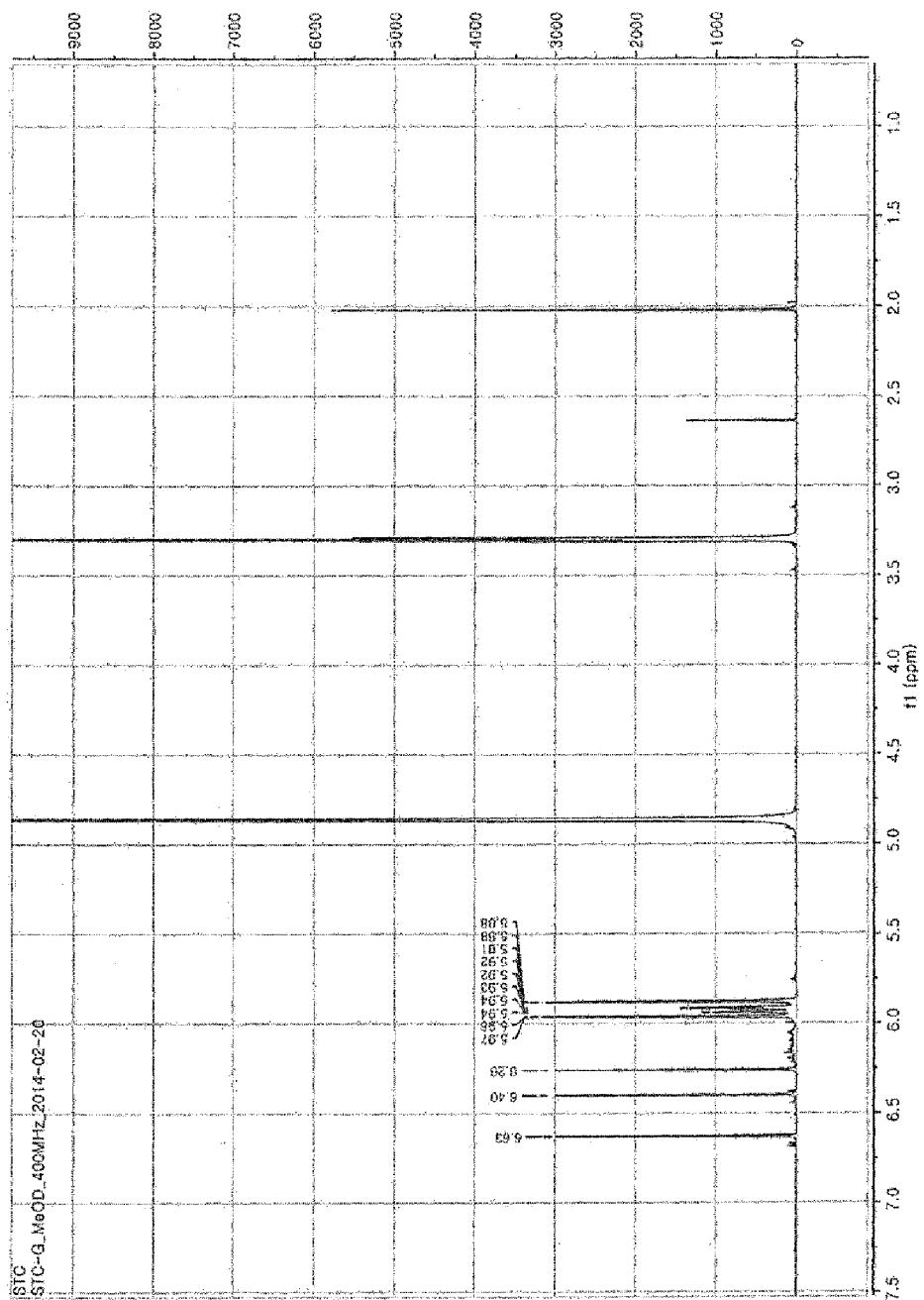
FIG. 9 illustrates a $^{1}$H-NMR spectrum result of phlorofucofuroeckol-A (PFF-A) represented by Chemical Formula 3.
Figure 10:
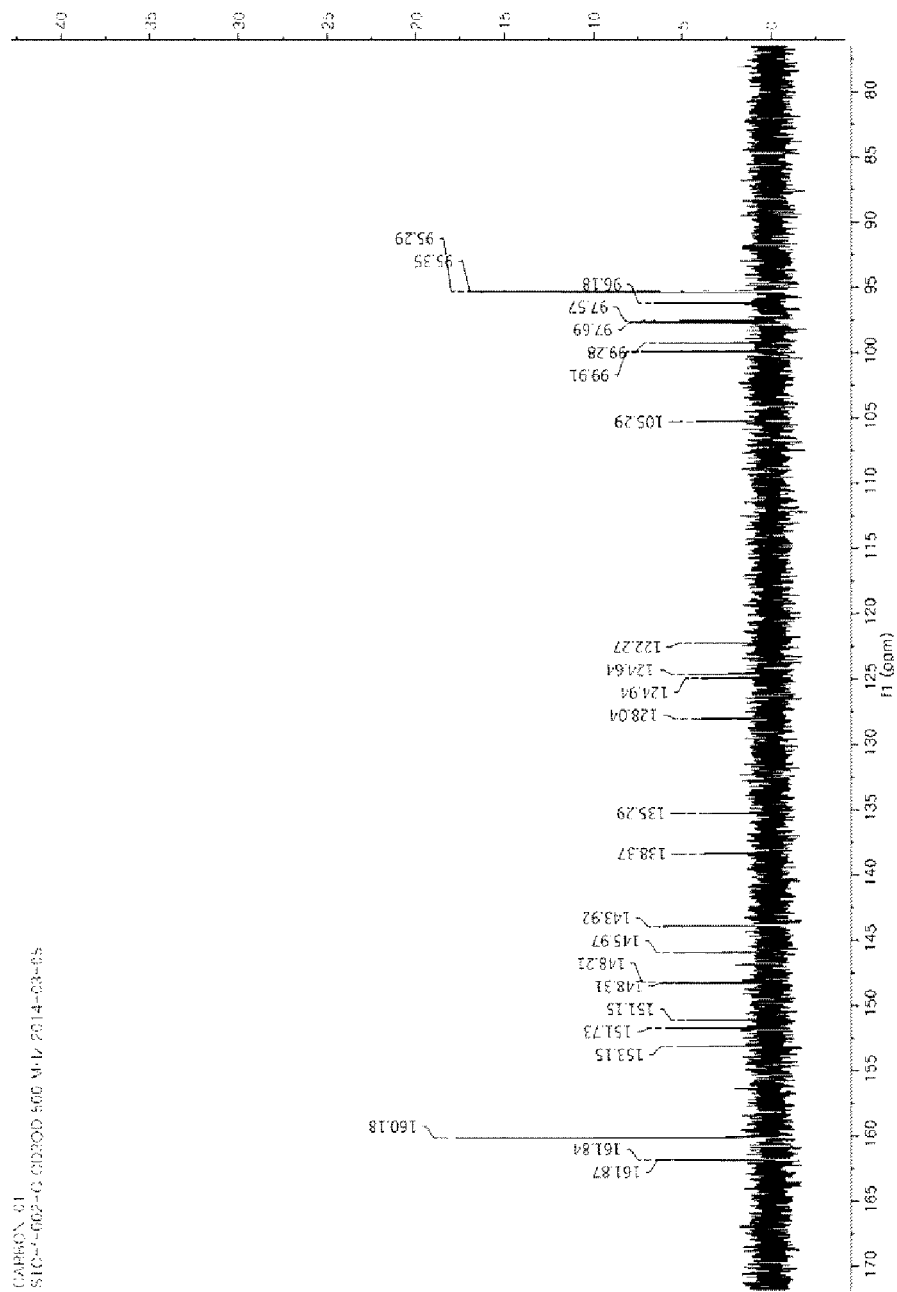
FIG. 10 illustrates a $^{13}$C-NMR spectrum result of phlorofucofuroeckol-A (PFF-A) represented by Chemical Formula 3.

Further, FIGS. 9 and 10 illustrate a 1H-NMR spectrum and a 13C-NMR spectrum of the PFF-A, respectively, and figures indicated in each peak corresponds to figures indicated in Chemical Formulas of FIGS. 9 and 10.

[Chemical Formula 4] 974-A

1) Molecular weight: 974.73
2) Molecular formula: C48H30O23
3) $^1$H NMR (400 MHz, MeOD) δ 6.63 (s, 1H), 6.40 (s, 1H), 6.25 (s, 1H), 6.20 (d, J=2.3 Hz, 1H), 6.18 (d, J=2.3 Hz, 1H), 6.12 (d, J=2.3 Hz, 1H, 6.04 (d, J=2.8 Hz, 1H), 5.92 (s, 2H), 5.925.91 (m, 1H), 5.90 (d, J=2.3 Hz, 1H), 5.87 (d, J=2.1 Hz, 2H), 5.74 (d, J=2.8 Hz, 1H).
4) $^{13}$C NMR (125 MHz, MeOD) δ 163.16, 162.88, 161.83, 160.16, 159.64, 159.54, 159.14, 159.09, 156.55, 156.49, 156.48, 153.85, 153.35, 152.26, 151.92, 151.77, 151.18, 148.21, 147.78, 145.82, 144.31, 138.15, 135.16, 127.62, 124.93, 124.90, 124.25, 124.22, 122.27, 119.40, 118.15, 105.22, 105.21, 102.62, 102.44, 99.91, 99.24, 98.61, 98.32, 97.68, 97.57, 96.34, 96.11, 95.28, 95.20, 94.37, 94.18.

Figure 11:
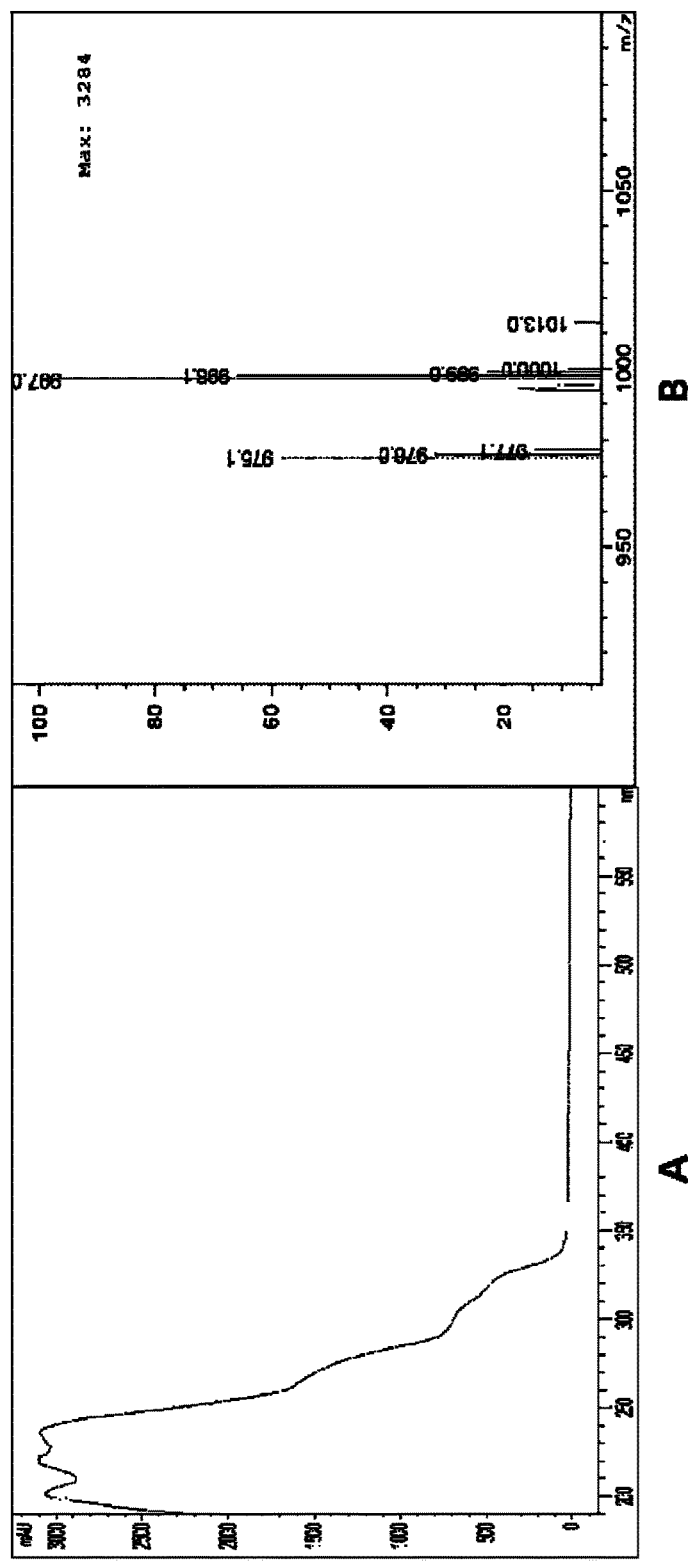
FIG. 11 illustrates a mass spectrum result of 974-A represented by Chemical Formula 4.
Figure 12:
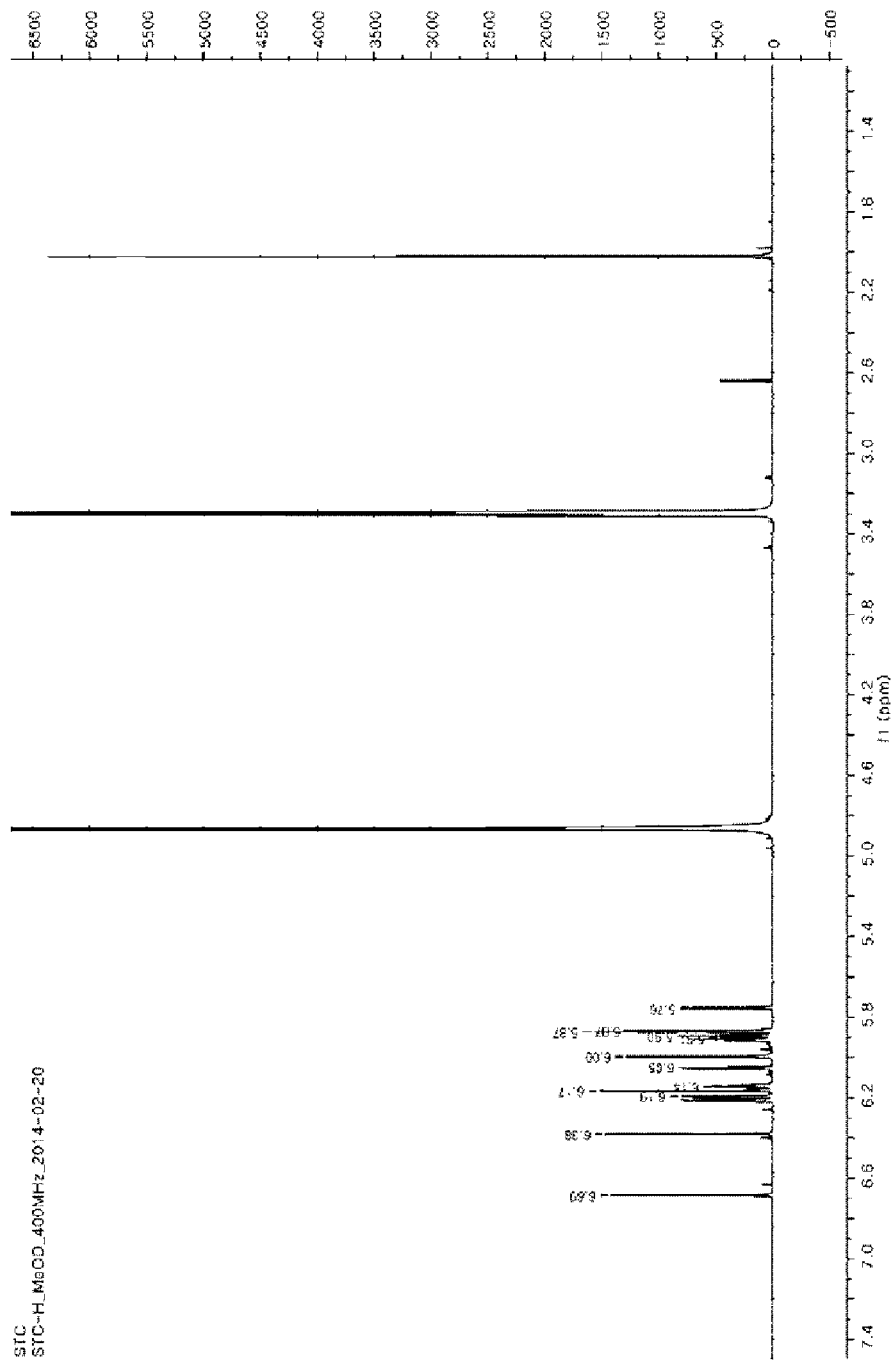
FIG. 12 illustrates a $^{1}$H-NMR spectrum result of 974-A represented by Chemical Formula 4.
Figure 13:
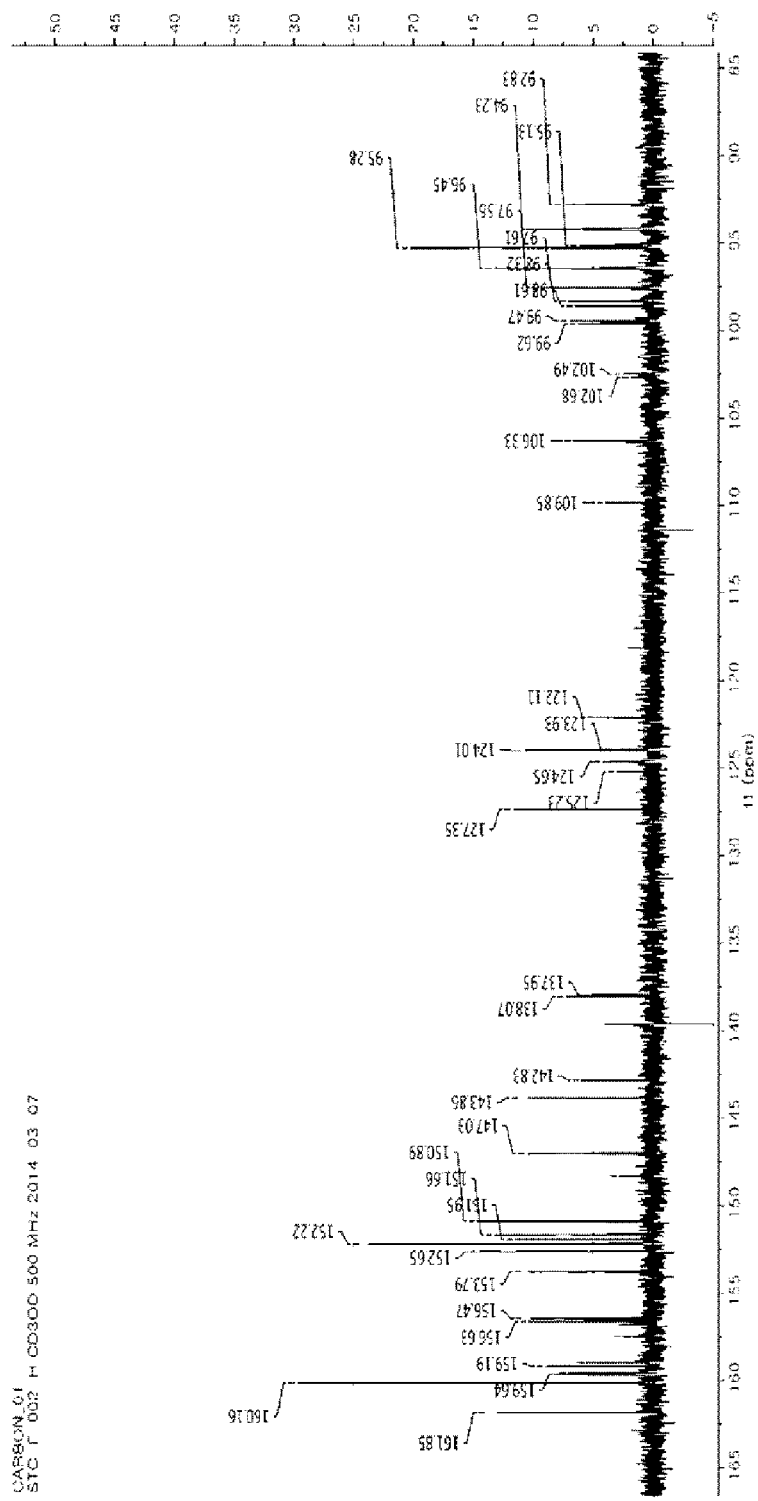
FIG. 13 illustrates a $^{13}$C-NMR spectrum result of 974-A represented by Chemical Formula 4.

FIG. 11 illustrates a mass spectrum of the 974-A. Further, FIGS. 12 and 13 illustrate a $^1$H-NMR spectrum and a 13C-NMR spectrum of the 974-A, respectively, and figures indicated in each peak corresponds to figures indicated in Chemical Formulas of FIGS. 12 and 13.

[Chemical Formula 5] 974-B

1) Molecular weight: 947.73
2) Molecular formula: C48H30O23
3) $^1$H NMR (400 MHz, MeOD) δ 6.69 (s, 1H), 6.38 (s, 1H), 6.21 (d, J=2.3 Hz, 1H), 6.19 (d, J=2.3 Hz, 1H), 6.17 (s, 1H), 6.14 (d, J=2.3 Hz, 1H), 6.05 (d, J=2.8 Hz, 1H), 6.00 (s, 2H), 5.91 (t, J=2.1 Hz, 1H), 5.89 (d, J=2.3 Hz, 1H), 5.87 (d, J=2.1 Hz, 2H), 5.76 (d, J=2.8 Hz, 1H).
4) $^{13}$C NMR (125 MHz, MeOD) δ 161.85, 160.16, 159.64, 159.53, 159.19, 158.97, 157.45, 156.81, 156.63, 156.47, 153.79, 152.65, 152.22, 151.95, 151.66, 150.89, 148.32, 147.03, 143.86, 142.83, 138.07, 137.95, 127.35, 125.23, 124.65, 124.01, 123.93, 122.11, 109.85, 106.33, 102.68, 102.49, 99.62, 99.47, 98.61, 98.32, 97.61, 97.56, 96.45, 95.28, 95.13, 94.23, 92.83.

Figure 14:
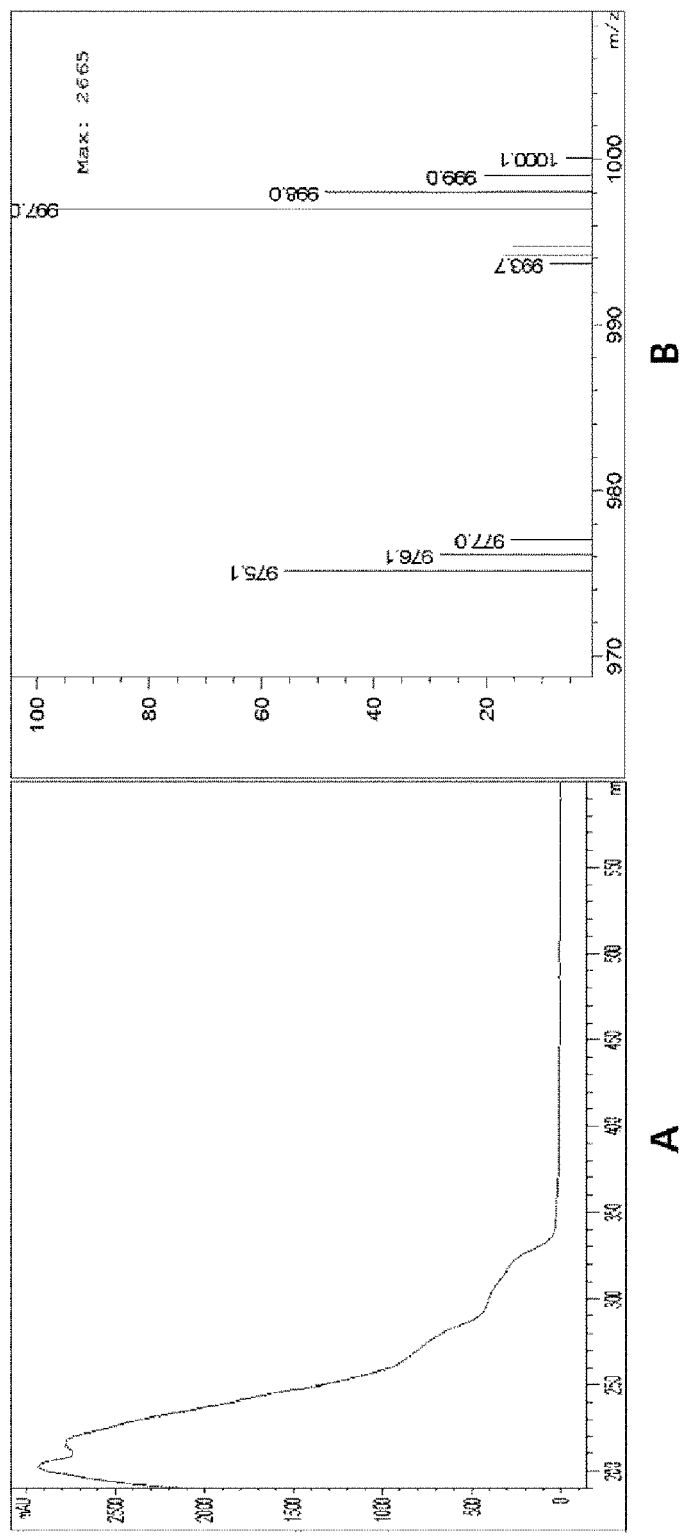
FIG. 14 illustrates a mass spectrum result of 974-B represented by Chemical Formula 4.
Figure 15:
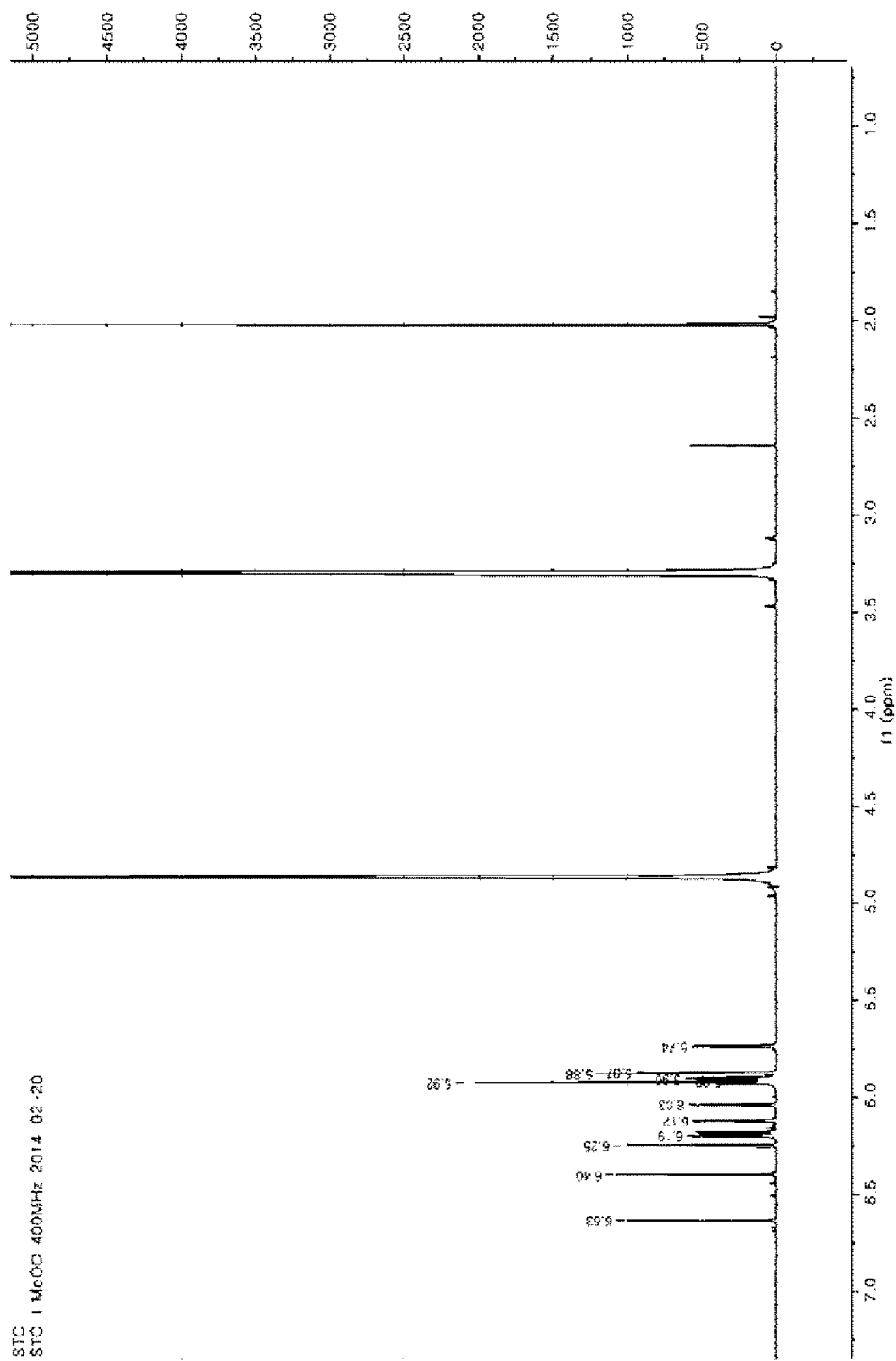
FIG. 15 illustrates a $^{1}$H-NMR spectrum result of 974-B represented by Chemical Formula 5.
Figure 16:
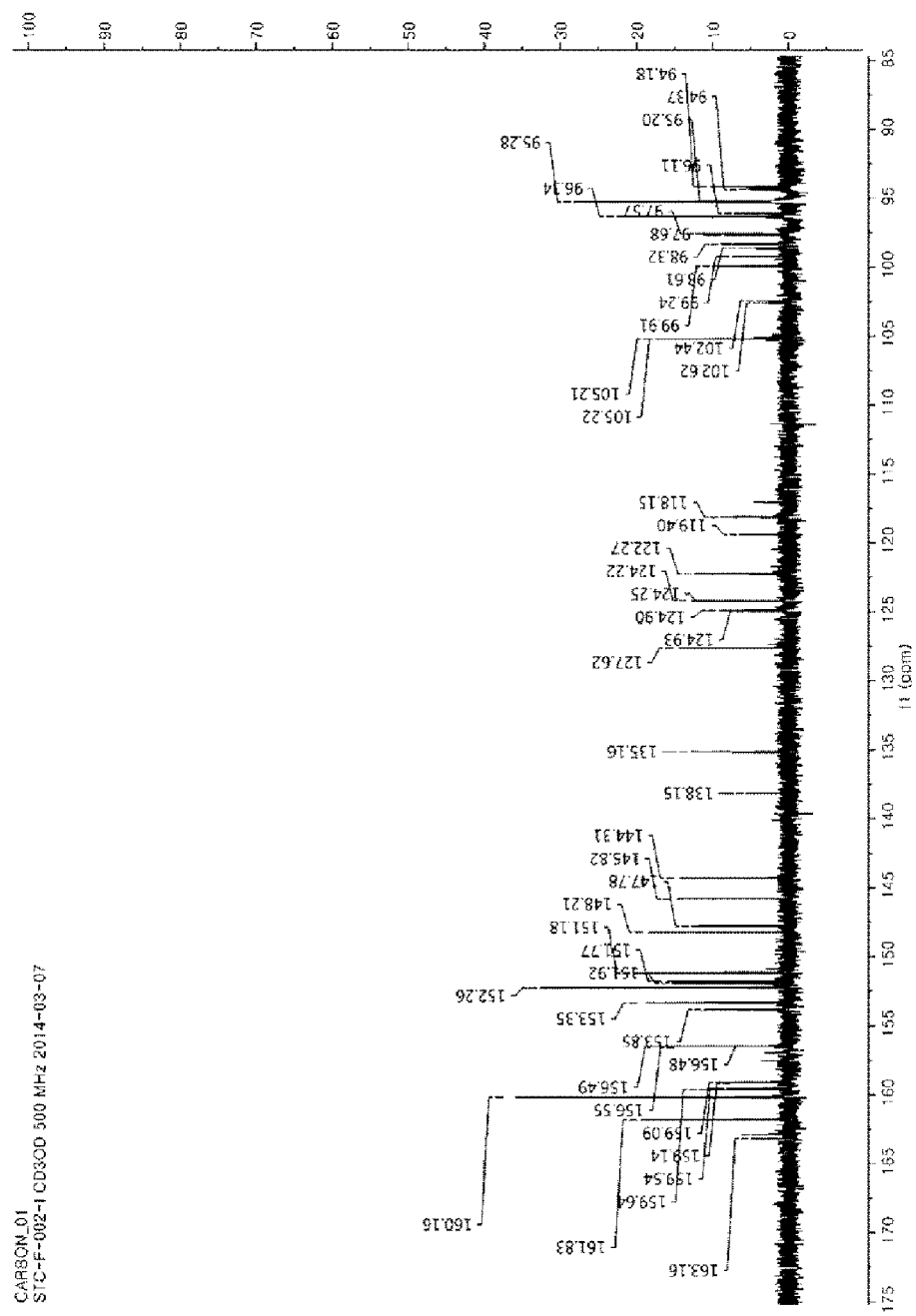
FIG. 16 illustrates a $^{13}$C-NMR spectrum result of 974-B represented by Chemical Formula 5.

FIG. 14 illustrates a mass spectrum of the 974-B. Further, FIGS. 15 and 16 illustrate a $^1$H-NMR spectrum and a 13C-NMR spectrum of the 974-B, respectively, and figures indicated in each peak corresponds to figures indicated in Chemical Formulas of FIGS. 15 and 16.

Example 2: Isolation and Incubation of Mesenchymal Stem Cells from Human Umbilical Cord Example 2-1: Extraction of Human Umbilical Cord An umbilical cord tissue was collected immediately after birth. The sample was first rinsed clean before being transferred to a laboratory and then immediately transferred to a 500 ml sterile glass bottle containing a F-12 medium added with a transfer medium (50 μg/ml penicillin and 50 μg/ml streptomycin (purchased from Invitrogen)). In the laboratory, stem cells were extracted in a flow hood of class 100 under a sterile condition. The sample was first transferred to a stainless steel container. The sample was washed with PBS several times and then the umbilical cord tissue sample was cut with a length of 2 cm and transferred to a cell culture dish with a diameter of 10 cm, and herein, additionally washed and treated with 70% ethanol for anti-infection, and then washed several times with PBS added with an antibiotic mixture (50 μg/ml penicillin and 50 μg/ml streptomycin (purchased from Invitrogen) until the solution was cleaned.

Example 2-2: Isolation and Incubation of Stem Cells from Human Umbilical Cord

In order to isolate Wharton's jelly (a substrate of umbilical cord) from blood vessel of the umbilical cord and other internal elements, cutting of the umbilical cord tissue was first performed. The Wharton's jelly isolated after removing the blood vessel was cut to small pieces with a size (0.5 cm×0.5 cm) for extraction of cells. Explanting was performed by adding the pieces of the umbilical cord Wharton's jelly in different tissue culture dishes which had cell culture conditions suitable for extraction of epithelial stem cells or mesenchymal stem cells.

For isolation/incubation of the mesenchymal stem cells, the explanted tissue was immersed in 5 ml DMEM (Dulbecco's modified eagle medium) F-12 (Gibco) added with 10% fetal bovine serum (FBS, Hyclone), 10% FBS, 100 unit/ml penicillin, and 50 μg/ml streptomycin and maintained at 37° C. in a carbon dioxide cell incubator. The medium was replaced every 3 or 4 days. The outgrowth of the cells was monitored by an optical microscope. The outgrown cells were treated with Trypsin (0.125% Trypsin/0.05% EDTA) for additional expansion and refrigeration (using DMEM/10% FBS).

The medium was replaced every 3 or 4 days. The outgrowth of the cells from the explanted tissue was monitored by an optical microscope.

For extraction of the mesenchymal stem cells, pellets of the cells were re-suspended and counted in the medium DMEM F-12 (Gibco), 10% FBS, 100 unit/ml penicillin, and 50 μg/ml streptomycin and inoculated on a 10 cm tissue culture dish at a density of $1\times10^6$ cells/dish. The medium was replaced every 3 or 4 days. The outgrowth and colony formation of the cells were monitored by an optical microscope. In approximately 90% cell number (confluence), the cells were sub-cultured as described above.

Experimental Example 1: Induction of Pluripotency Stem Cells from Mesenchymal Stem Cells Experimental Example 1-1: Preparation of Pluripotency Stem Cells of Mesenchymal Stem Cells Derived from Human According to Concentration of Phlorotannin Fraction An experiment for measuring induction ability of pluripotency stem cells from mesenchymal stem cells derived from human umbilical cord according to a concentration of the phlorotannin fraction prepared in Example 1-1 was performed. In a control group, DMEM F-12 (Gibco) as a dedicated medium of MSC, 10% FBS, 100 unit/ml penicillin, and 50 μg/ml streptomycin were used as a basic medium (Normal), and in an experimental group, mesenchymal stem cells derived from human which was subjected to three sub-cultures were used and phlorotannin fractions having concentrations of 1 μg/ml, 20 μg/ml, 50 μg/ml, 100 μg/ml, 400 μg/ml, 800 μg/ml, and 1000 μg/ml and 0.1 v/v % energy water (purified deionized water containing $SiO_2$, $Al_2O_3$, $TiO_3$, $Fe_2O_3$, CaO, $Na_2O$, $K_2O$, and LiO, STC) were added in the medium. The mesenchymal stem cells derived from human umbilical cord were isolated and washed and mononuclear cells were inoculated in a 6-well plate (dish) with $1\times10^4$ cells and maintained and incubated at 37° C. and 5% $CO_2$.

With respect to the pluripotency stem cells induced by the method of the present invention, whether to express stage-specific embryonic antigen4 (SSEA-4), alkaline phosphatase (AP), OCT4, and SOX2 as specific proteins to embryonic stem cells was analyzed by using antibodies thereof and an immunochemical staining method. During the staining process, cells were first fixed by using 4% paraformaldehyde and washed with PBS, and blocked with a 1% BSA solution. The cells were treated with primary antibodies for OCT4, SOX2, and SSEA-4 and reacted at 4° C. for 18 hours, and then washed with PBS, treated with secondary antibodies with fluorescence (FITC) to the primary antibodies, and reacted at room temperature for 1 hour. The cells were washed with PBS and then the expression was analyzed by using a confocal microscope. The BF meant a bright field and the second drawing illustrated a staining result for protein expression, and the third drawing illustrated the combined two drawings (see FIGS. 19A, 19B, 20A, and 20B). AP staining was performed with an alkaline phosphatase cell-permeable fluorogenic substrate dye, the AP fluorogenic dye was diluted in a DMEM F-12 culture solution to be treated in colonies, and then reacted for 20 to 30 min, washed with the DMEM F-12 culture solution two times, and the expression was analyzed by using a confocal microscope, and the result was illustrated in FIG. 17.

Figure 18:
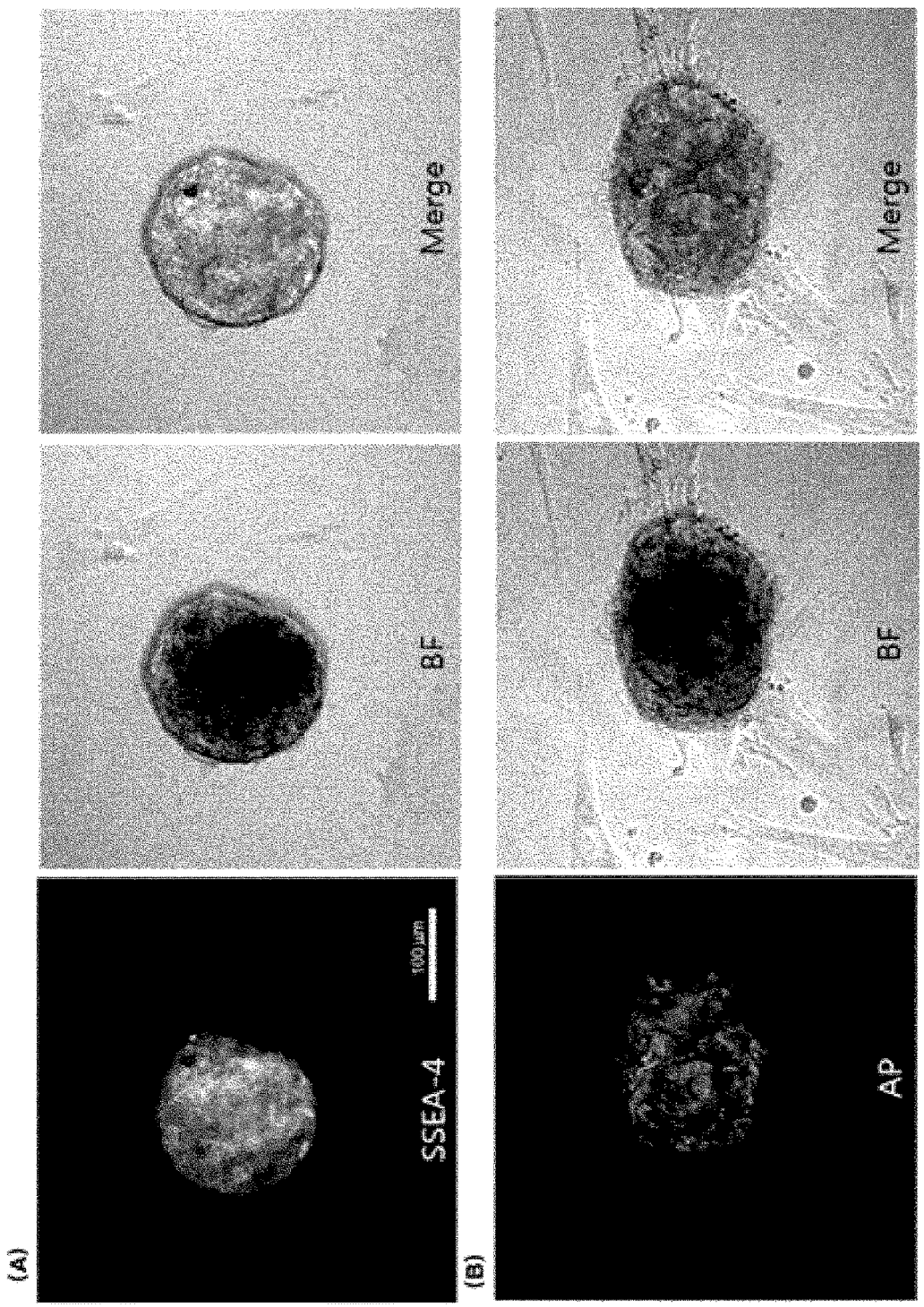
FIG. 18 verifies that the cells induced by the method of the present invention (Experimental Example 1-1) are pluripotency stem cells by using expression of SSEA-4 and alkaline phosphatase which are pluripotency stem cell-specific proteins.
Figure 19:
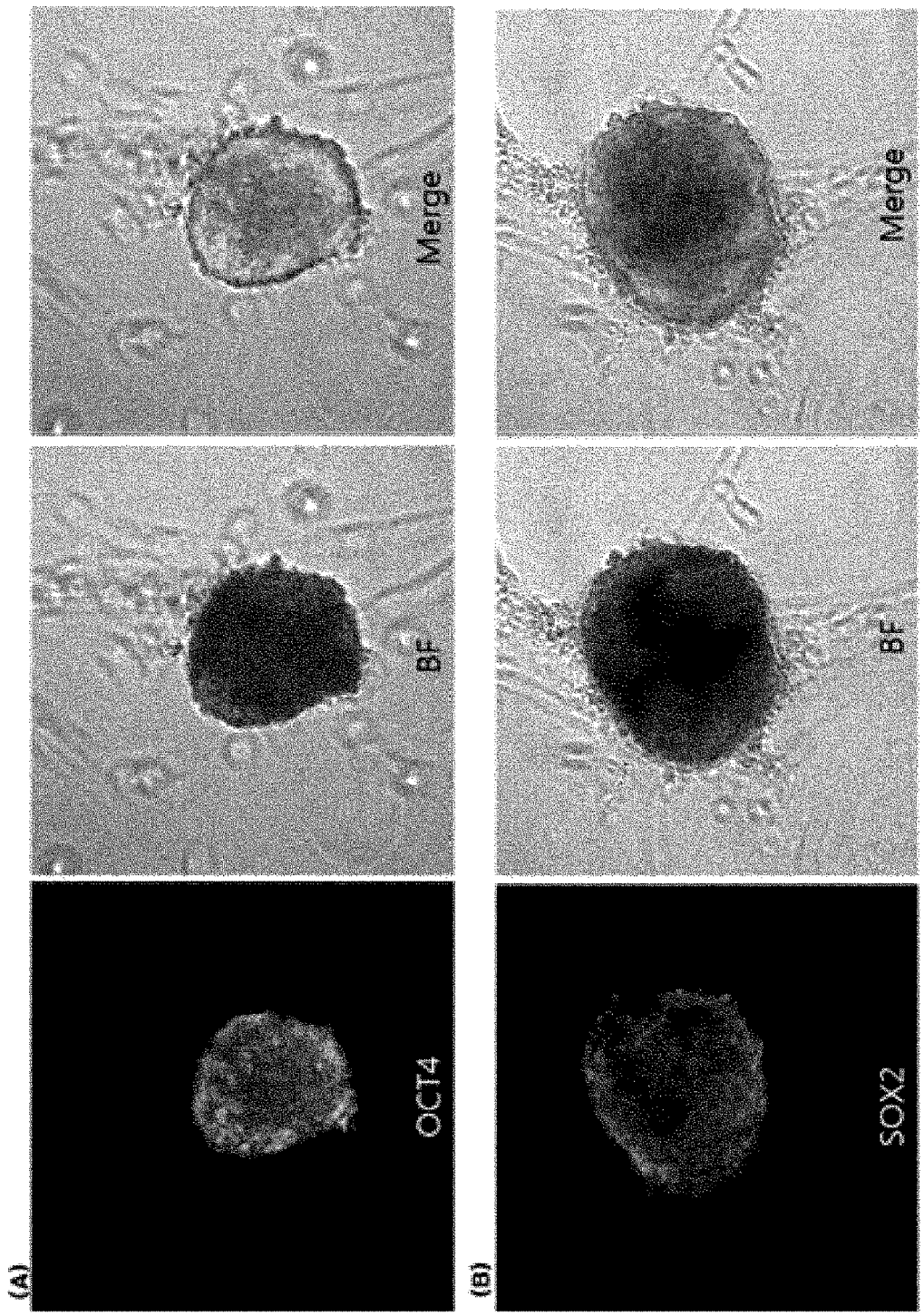
FIG. 19 verifies that the cells induced by the method of the present invention (Experimental Example 1-1) are pluripotency stem cells by using expression of OCT4 and SOX2 which are pluripotency stem cell-specific genes.
Figure 20:
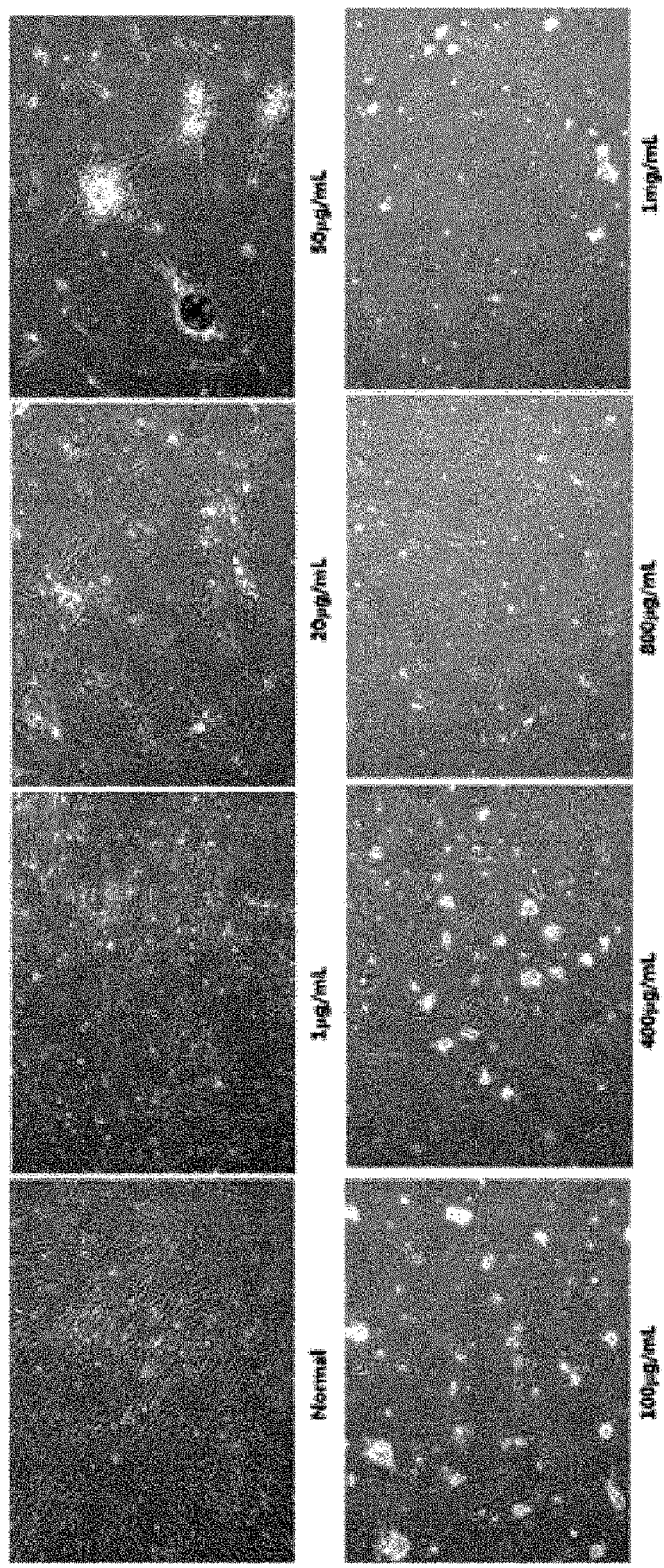
FIG. 20 illustrates formation of pluripotency stem cell colonies induced according to a concentration by treating a compound in a phlorotannin fraction by using a method (Experimental Example 1-2) of the present invention.

As a result, in the experimental group, only when the concentration of the phlorotannin fraction was 10 to 500 μg/ml, it was observed that the colonies were formed after 10 days (see FIG. 17) and it was verified that only the colonies were stained by OCT4, SOX2, SSEA-4, and AP as pluripotency stem cell-specific markers to be the pluripotency stem cells (see FIGS. 18 and 19).

Experimental Example 1-2: Preparation of Pluripotency Stem Cells of Mesenchymal Stem Cells Derived from Human According to Concentration of Compound in Phlorotannin Fraction An experiment for measuring induction ability of pluripotency stem cells from mesenchymal stem cells derived from human according to a concentration of compound 1 among the compounds isolated in Example 1-2 was performed. In a control group, DMEM F-12 (Gibco) as a dedicated medium of MSC, 10% FBS, 100 unit/ml penicillin, and 50 μg/ml streptomycin were used as a basic medium (Normal), and in an experimental group, mesenchymal stem cells derived from human umbilical cord which was subjected to three sub-cultures were used, and bieckol compound 1 represented by Chemical Formula 1 having concentrations of 1 μg/ml, 20 μg/ml, 50 μg/ml, 100 μg/ml, 400 μg/ml, 800 μg/ml, and 1000 μg/ml and 0.1 v/v % energy water (purified deionized water containing $SiO_2$, $Al_2O_3$, $TiO_3$, $Fe_2O_3$, CaO, $Na_2O$, $K_2O$, and LiO, STC) were added in the medium. The mesenchymal stem cells derived from human umbilical cord were isolated and washed and mononuclear cells were inoculated in a 6-well plate (dish) with $1\times10^4$ cells and maintained and incubated at 37° C. and 5% $CO_2$.

With respect to the induced pluripotency stem cells, whether to express stage-specific embryonic antigen4 (SSEA-4), alkaline phosphatase, OCT4, and SOX2 as specific proteins to embryonic stem cells was analyzed by using antibodies thereof and an immunochemical staining method. During the staining process, cells were first fixed by using 4% paraformaldehyde and washed with PBS, and blocked with a 1% BSA solution. The cells were treated with primary antibodies for OCT4, SOX2, and SSEA-4 and reacted at 4° C. for 18 hours, and then washed with PBS, treated with secondary antibodies with fluorescence (FITC) to the primary antibodies, and reacted at room temperature for 1 hour. The cells were washed with PBS and then the expression was analyzed by using a confocal microscope, and the result there of was illustrated in FIG. 20. The BF meant a bright field and the second drawing illustrated a staining result for protein expression, and the third drawing illustrated the combined two drawings (see FIGS. 21A, 21B, 22A, and 22B).

AP staining was performed with an alkaline phosphatase cell-permeable fluorogenic substrate dye, the AP fluorogenic dye was diluted in a DMEM F-12 culture solution to be treated in colonies, and then reacted for 20 to 30 min, washed with the DMEM F-12 culture solution two times, and the expression was analyzed by using a confocal microscope, and the result was illustrated in FIG. 22B.

Figure 21:
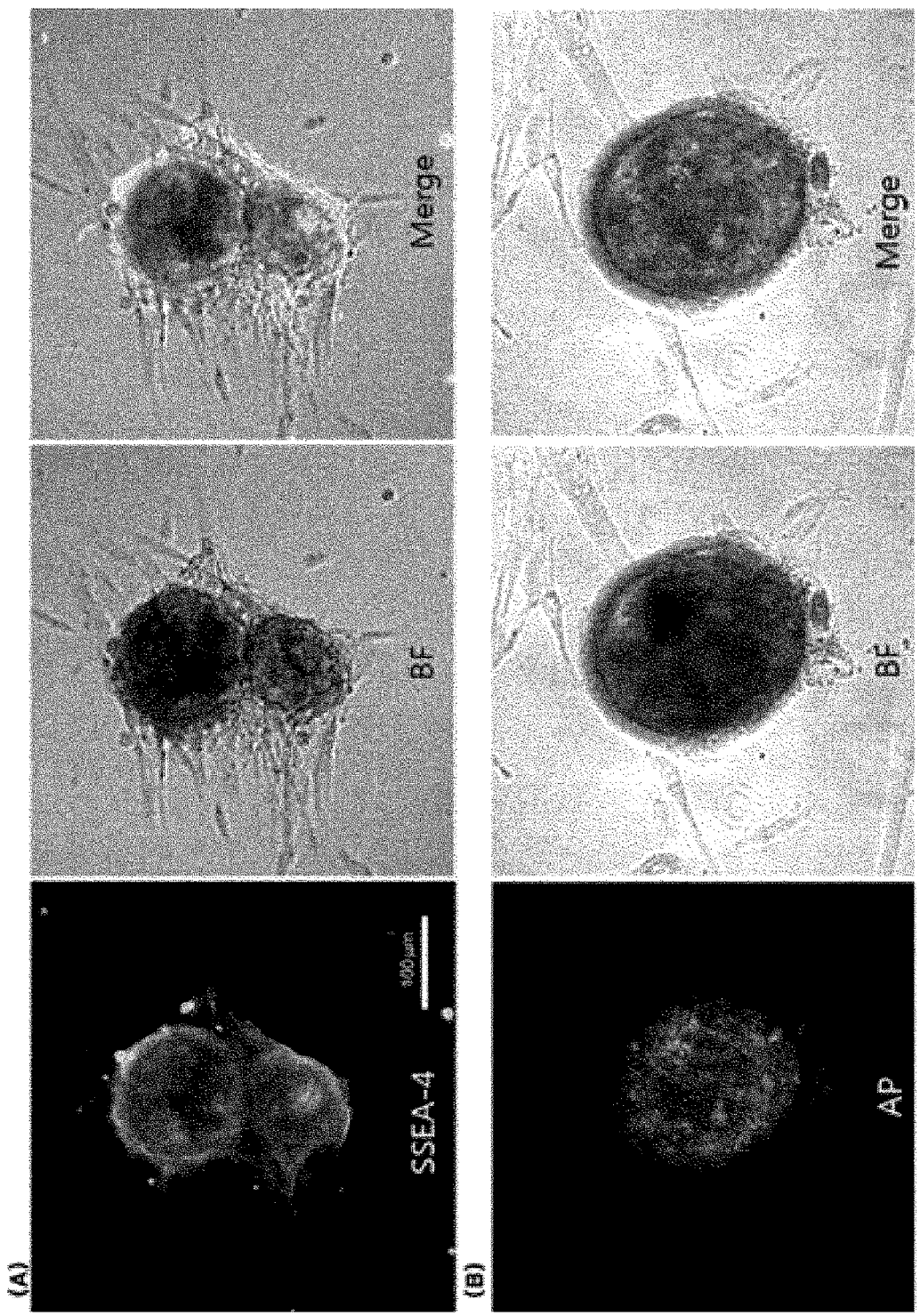
FIG. 21 verifies that the cells induced by the method of the present invention (Experimental Example 1-2) are pluripotency stem cells by using expression of SSEA-4 and alkaline phosphatase which are pluripotency stem cell-specific proteins.
Figure 22:
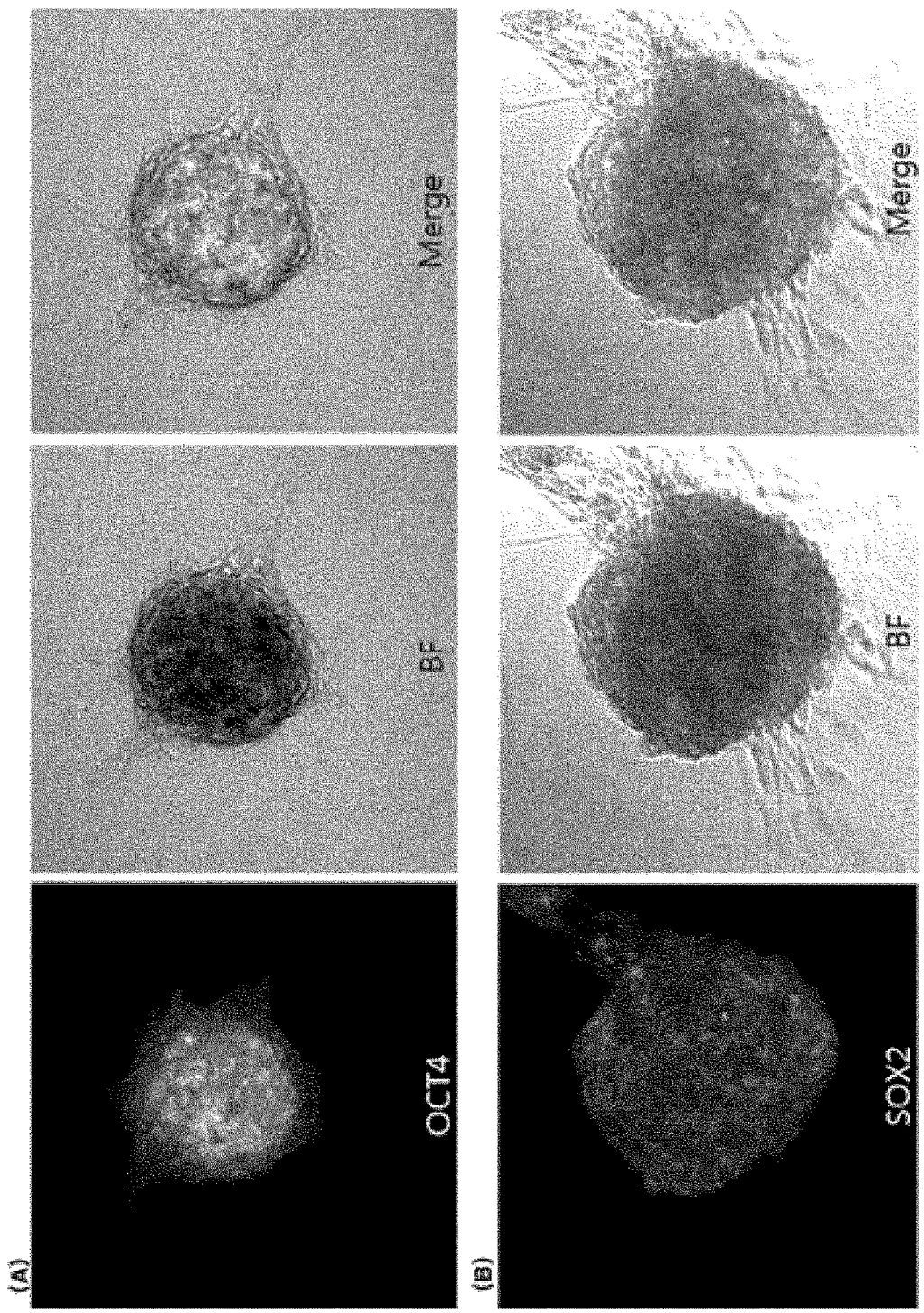
FIG. 22 verifies that the cells induced by the method of the present invention (Experimental Example 1-2) are pluripotency stem cells by using expression of OCT4 and SOX2 which are pluripotency stem cell-specific genes.

As a result, in the experimental group, only when the concentration of the bieckol compound 1 represented by Chemical Formula 1 was 50 μg/ml and 100 μg/ml, it was observed that the colonies were formed after 14 days (see FIG. 20) and it was verified that only the colonies were stained by OCT4, SOX2, SSEA-4, and AP as pluripotency stem cell-specific markers to be the pluripotency stem cells (see FIGS. 21 and 22).

The invention claimed is:

1. A method for preparing induced pluripotency stem cells, comprising the steps of:
   (a) adding a fraction containing phlorotannin in a cell culture medium; and
   (b) culturing mesenchymal stem cells in the medium to dedifferentiate into induced pluripotent stem cells.

2. The method of claim 1, wherein the fraction containing phlorotannin is a bieckol compound represented by the following Chemical Formula 1 or salts thereof

[Chemical Formula 1]

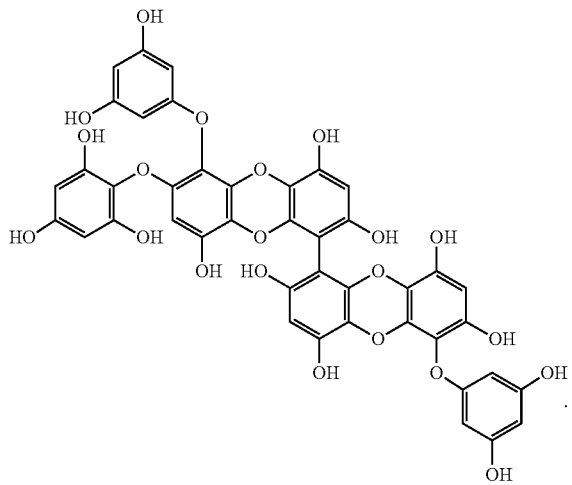

3. The method of claim 1, wherein the fraction containing phlorotannin is extracted and isolated from one type of brown algae selected from the group consisting of *Ecklonia cava, Dictyopteris prolifera Okamura, Dictyota dichotoma Lamouroux, Sargassum horneri C. Agardh, Sargassum patens C. Agardh*, and *Ishige okamurae Yendo*, or artificially synthesized.

4. The method of claim 1, wherein the fraction containing phlorotannin is included in the amount of 10 to 500 μg/ml with respect to the medium composition.

5. The method of claim 1, wherein the medium further contains 0.01-10% (v/v) of purified deionized water containing $SiO_2$, $Al_2O_3$, $TiO_3$, $Fe_2O_3$, CaO, $Na_2O$, $K_2O$, and LiO.

6. The method of claim 1, wherein the medium is selected from the group consisting of DMEM (Dulbecco's Modified Eagle's Medium), MEM (Minimal Essential Medium), BME (Basal Medium Eagle), RPMI 1640, F-10, F-12, DMEM F-12, α-MEM (α-Minimal Essential Medium), G-MEM (Glasgow's Minimal Essential Medium), IMDM (Iscove's Modified Dulbecco's Medium) and MacCoy's 5A medium.

* * * * *